US008961995B2

(12) United States Patent
Frolov et al.

(10) Patent No.: US 8,961,995 B2
(45) Date of Patent: Feb. 24, 2015

(54) METHODS AND COMPOSITIONS FOR ALPHAVIRUS REPLICONS

(71) Applicant: UAB Research Foundation, Birmingham, AL (US)

(72) Inventors: Ilya Frolov, Birmingham, AL (US); Elena Frolova, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/789,215

(22) Filed: Mar. 7, 2013

(65) Prior Publication Data
US 2014/0079734 A1    Mar. 20, 2014

Related U.S. Application Data

(60) Provisional application No. 61/703,529, filed on Sep. 20, 2012.

(51) Int. Cl.
| | | |
|---|---|---|
| C07K 14/18 | (2006.01) | |
| C12N 15/86 | (2006.01) | |
| C12N 7/01 | (2006.01) | |
| C12N 15/40 | (2006.01) | |
| A61K 35/76 | (2006.01) | |
| A61K 39/00 | (2006.01) | |
| C12N 7/00 | (2006.01) | |
| A61K 39/12 | (2006.01) | |

(52) U.S. Cl.
CPC ............... *C12N 15/86* (2013.01); *A61K 39/12* (2013.01); *C12N 2770/00* (2013.01); *C12N 2770/36011* (2013.01); *C12N 2770/36132* (2013.01); *C12N 2770/36134* (2013.01); *C12N 2770/36111* (2013.01); *C12N 2770/36151* (2013.01)
USPC .................... 424/218.1; 424/204.1; 424/93.1; 424/184.1; 536/23.4; 435/320.1; 435/235.1; 435/71.1; 435/70.1

(58) Field of Classification Search
CPC .............. A61K 2039/53; A61K 39/12; A61K 2039/5258; A61K 2039/5254; A61K 2039/55516; A61K 38/162; C07K 14/005; C12N 15/86; C12N 2770/36143; C12N 15/62; C12N 2770/36121; C12N 2770/36162; C12N 2310/351
See application file for complete search history.

(56) References Cited

U.S. PATENT DOCUMENTS

| | | | | |
|---|---|---|---|---|
| 5,843,723 | A  * | 12/1998 | Dubensky et al. | ............ 435/69.3 |
| 6,465,634 | B1 * | 10/2002 | Dubensky et al. | ......... 536/23.72 |
| 6,943,015 | B2 | 9/2005 | Frolov et al. | |
| 7,332,322 | B2 | 2/2008 | Frolov et al. | |
| 8,093,021 | B2 * | 1/2012 | Hurtado et al. | ............... 435/91.4 |
| 8,252,574 | B2 | 8/2012 | Mason et al. | |
| 8,426,188 | B2 | 4/2013 | Weaver et al. | |
| 8,614,082 | B2 | 12/2013 | Frolov et al. | |
| 2006/0251678 | A1 * | 11/2006 | Frolov et al. | ............... 424/204.1 |
| 2009/0155301 | A1 * | 6/2009 | Mason et al. | ............... 424/199.1 |
| 2010/0015179 | A1 * | 1/2010 | Frolov et al. | ............... 424/205.1 |
| 2010/0120897 | A1 * | 5/2010 | Hurtado et al. | ............. 514/44 R |
| 2011/0027183 | A1 * | 2/2011 | Mier et al. | ...................... 424/9.1 |
| 2011/0207233 | A1 * | 8/2011 | Shimonaka | ................... 436/501 |
| 2012/0100181 | A1 | 4/2012 | Frolov et al. | |
| 2013/0023031 | A1 | 1/2013 | Mason et al. | |
| 2014/0010841 | A1 | 1/2014 | Weaver et al. | |
| 2014/0065178 | A1 | 3/2014 | Frolov et al. | |

OTHER PUBLICATIONS

Michel G, Petrakova O, Atasheva S, Frolov I. Adaptation of Venezuelan equine encephalitis virus lacking 51-nt conserved sequence element to replication in mammalian and mosquito cells. Virology. Jun. 5, 2007;362(2):475-87. Epub Feb. 12, 2007.*

Kulasegaran-Shylini R, Atasheva S, Gorenstein DG, Frolov I. Structural and functional elements of the promoter encoded by the 5' untranslated region of the Venezuelan equine encephalitis virus genome. J Virol. Sep. 2009;83(17):8327-39. Epub Jun. 10, 2009.*

Shirako Y, Strauss EG, Strauss JH. Modification of the 5' terminus of Sindbis virus genomic RNA allows nsP4 RNA polymerases with nonaromatic amino acids at the N terminus to function in RNA replication. J Virol. Feb. 2003;77(4):2301-9.*

Perri S, Greer CE, Thudium K, Doe B, Legg H, Liu H, Romero Re, Tang Z, Bin Q, Dubensky TW Jr, Vajdy M, Otten GR, Polo JM. An alphavirus replicon particle chimera derived from venezuelan equine encephalitis and sindbis viruses is a potent gene-based vaccine delivery vector. J Virol. Oct. 2003;77(19):10394-403.*

Frolov I, Frolova E, Schlesinger S. Sindbis virus replicons and Sindbis virus: assembly of chimeras and of particles deficient in virus RNA. J Virol. Apr. 1997;71(4):2819-29.*

Volkova E, Gorchakov R, Frolov I. The efficient packaging of Venezuelan equine encephalitis virus-specific RNAs into viral particles is determined by nsP1-3 synthesis. Virology. Jan 20, 2006;344(2):315-27. Epub Oct. 18, 2005.*

Atasheva et al., "Pseudoinfectious Venezuelan Equine Encephalitis Virus: a New Means of Alphavirus Attenuation" *Journal of Virology* 87(4): 2023-2035 (2013).

Garmashova et al., "The Old World and New World Alphaviruses Use Different Virus-Specific Proteins for Induction of Transcriptional Shutoff" *Journal of Virology* 81(5):2472-2484 (2007).

Kim et al., "Conservation of a Packaging Signal and the Viral Genome RNA Packaging Mechanism in Alphavirus Evolution" *Journal of Virology* 85(16):8022-8036 (2011).

* cited by examiner

*Primary Examiner* — Benjamin P Blumel
*Assistant Examiner* — Rachel Gill
(74) *Attorney, Agent, or Firm* — Myers Bigel Sibley & Sajovec, P.A.

(57) ABSTRACT

The present invention provides alphavirus replicons and methods of their use in producing heterologous protein.

19 Claims, 7 Drawing Sheets

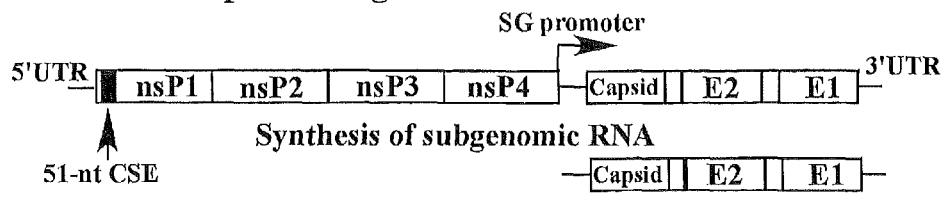
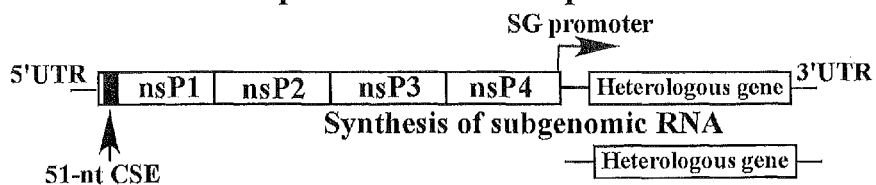
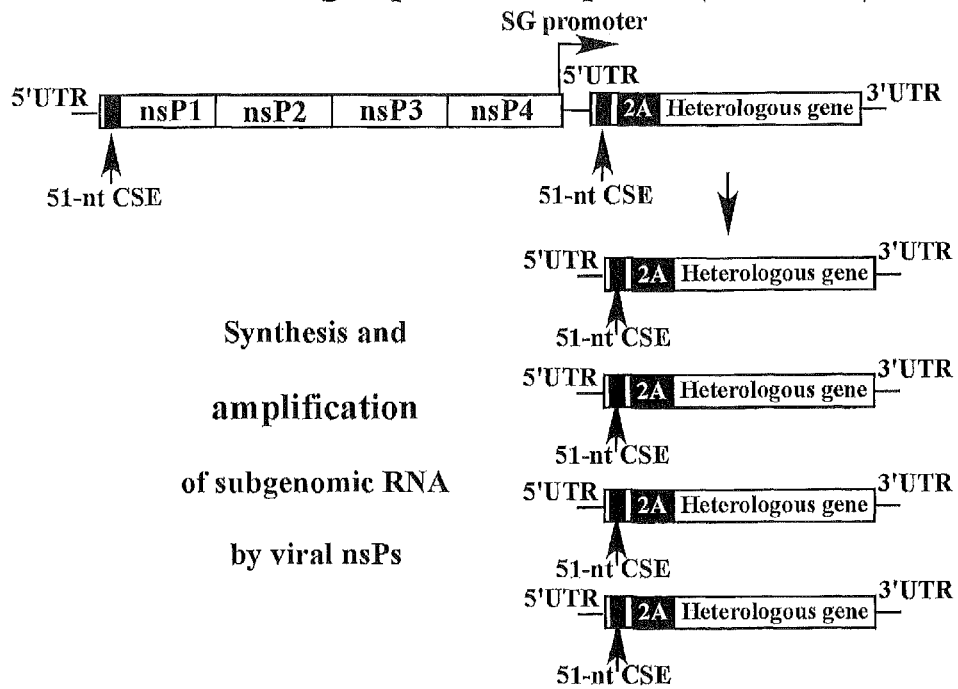
FIG. 1

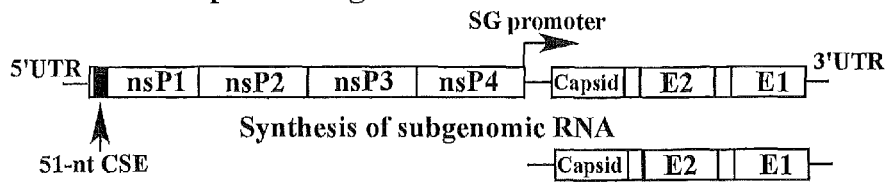
Natural alphavirus genome
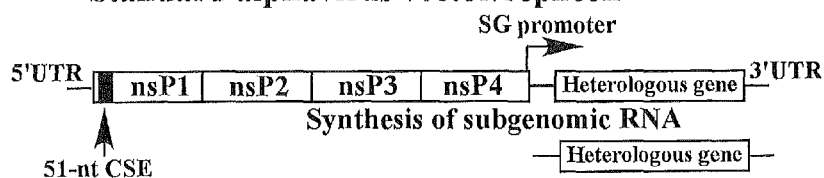
Standard alphavirus vector/replicon
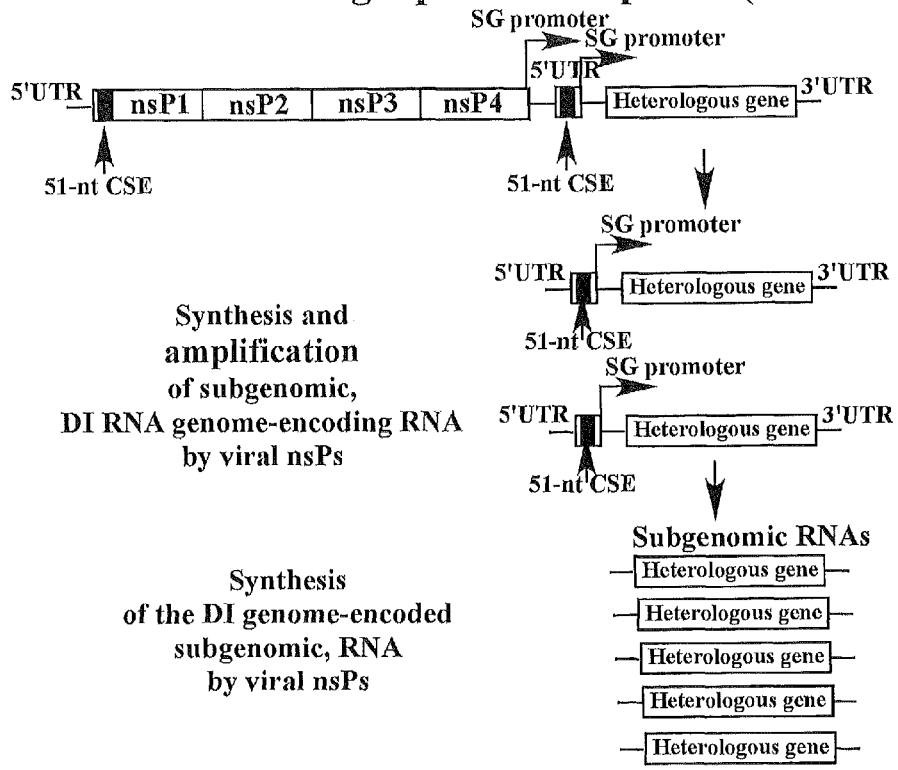
DI RNA-encoding alphavirus replicon (Version 2)
FIG. 2

Natural alphavirus genome

5'UTR — [nsP1 | nsP2 | nsP3 | nsP4] — [Capsid | E2 | E1] — 3'UTR
↑ 51-nt CSE
SG promoter
Synthesis of subgenomic RNA
— [Capsid | E2 | E1] —

Standard alphavirus vector/replicon

5'UTR — [nsP1 | nsP2 | nsP3 | nsP4] — [Heterologous gene] — 3'UTR
↑ 51-nt CSE
SG promoter
Synthesis of subgenomic RNA
— [Heterologous gene] —

DI RNA-encoding alphavirus replicon (Version 3)

5'UTR — [nsP1 | nsP2 | nsP3 | nsP4] — [5'UTR or tRNA | 2A | Heterologous gene] — 3'UTR
↑ 51-nt CSE                              ↑ 51-nt CSE
SG promoter   SG promoter
Translational enhancer Synthesis and amplification of subgenomic, DI RNA genome-encoding RNA by viral nsPs 5'UTR or tRNA — [2A | Heterologous gene] — 3'UTR
↑ 51-nt CSE
SG promoter
Translational enhancer 5'UTR or tRNA — [2A | Heterologous gene] — 3'UTR
↑ 51-nt CSE
Translational enhancer Synthesis of the DI genome-encoded subgenomic, RNA by viral nsPs

Subgenomic RNAs

— [2A | Heterologous gene] —
Translational enhancer

— [2A | Heterologous gene] —
Translational enhancer

— [2A | Heterologous gene] —
Translational enhancer

— [2A | Heterologous gene] —
Translational enhancer

METHODS AND COMPOSITIONS FOR ALPHAVIRUS REPLICONS

PRIORITY STATEMENT

This application claims the benefit, under 35 U.S.C. §119 (e), of U.S. Provisional Patent Application Ser. No. 61/703,529 filed Sep. 20, 2012, the entire contents of which are incorporated by reference herein.

STATEMENT OF GOVERNMENT SUPPORT

This invention was made with government support under Grants No. AI070207 and AI093592 awarded by the National Institutes of Health. The U.S. Government has certain rights in this invention.

FIELD OF THE INVENTION

The present invention relates to alphavirus replicons and their use in vaccine and protein production.

BACKGROUND OF THE INVENTION

Alphaviruses have become an attractive system for delivery and expression of new genetic information and for development of new vaccines against a wide variety of viral and bacterial infections. Their applications are based on efficient amplification of viral genomes upon their delivery into cells and the ability to produce high levels of messenger RNAs, which typically encode a protein of interest. However, previous alphavirus vectors were designed based on the natural viral genome strategy, which has evolved for efficient virus replication in vertebrates and mosquitoes and for optimal disease development, but not for optimal expression of new genetic information.

The present invention overcomes previous shortcomings in the art by providing recombinant alphavirus replicons with improved protein production efficiency.

SUMMARY OF THE INVENTION

In one aspect, the present invention provides a recombinant replicon nucleic acid comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51 nucleotide conserved sequence element (51-nt CSE); e) a nucleic acid sequence encoding a protease; f) a nucleic acid sequence encoding a heterologous protein; and g) a nucleic acid sequence encoding an alphavirus 3' untranslated region (3' UTR).

In a further aspect, the present invention provides a recombinant replicon nucleic acid comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding a first alphavirus subgenomic promoter; d) a nucleic acid sequence encoding a second alphavirus 5' untranslated region (5' UTR) and a 51 nucleotide conserved sequence element (51-nt CSE); e) a nucleic acid sequence encoding a second alphavirus subgenomic promoter; f) a nucleic acid sequence encoding a heterologous protein; and g) a nucleic acid sequence encoding an alphavirus 3' untranslated region (3' UTR).

In an additional aspect, the present invention provides a recombinant replicon nucleic acid comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding a first alphavirus subgenomic promoter; d) a nucleic acid sequence encoding a second alphavirus 5' untranslated region (5' UTR) or a modified 5' UTR comprising a cellular Asp tRNA sequence and a 51 nucleotide conserved sequence element (51-nt CSE); e) a nucleic acid sequence encoding a second alphavirus subgenomic promoter; f) a nucleic acid sequence encoding a translational enhancer derived from an Old World alphavirus such as, e.g., Sindbis, Semliki Forest, Ross River or other Old World alphavirus; g) a nucleic acid sequence encoding a protease; h) a nucleic acid sequence encoding a heterologous protein; and i) a nucleic acid sequence encoding an alphavirus 3' untranslated region (3' UTR).

The present invention also provides a method of producing a heterologous protein in a cell, comprising introducing the recombinant replicon nucleic acid of this invention into the cell under conditions whereby the nucleic acid sequence encoding the heterologous protein is expressed, thereby producing the heterologous protein in the cell.

In yet further aspects, the present invention provides a method eliciting an immune response to a heterologous protein in a subject, comprising administering to the subject an immunogenic amount of a recombinant replicon nucleic acid of this invention, thereby eliciting an immune response to the heterologous protein encoded by the recombinant replicon nucleic acid.

Also provided herein is a method of delivering a therapeutic heterologous protein and/or functional RNA to a subject, comprising administering to the subject a recombinant replicon nucleic acid of this invention, wherein the replicon nucleic acid encodes a therapeutic heterologous protein and/or functional RNA, thereby delivering a therapeutic heterologous protein and/or functional RNA to the subject.

An additional aspect of this invention is a method of making infectious, defective alphavirus particles, by 1) introducing into a cell the following: (i) a recombinant replicon nucleic acid of this invention; and (ii) one or more helper nucleic acids encoding alphavirus structural proteins, wherein the one or more helper nucleic acids produce all of the alphavirus structural proteins, and b) producing said alphavirus particles by the cell.

BRIEF DESCRIPTION OF THE DRAWINGS

FIG. 1. The schematic representation of the alphavirus replicon, encoding DI RNA, which is amplified by the nonstructural viral proteins (nsP1-4).

FIG. 2. The schematic representation of the alphavirus replicon, encoding subgenomic RNA-containing DI RNA, which is amplified by the nonstructural proteins (nsP1-4).

FIG. 3. The schematic representation of the alphavirus replicon, encoding subgenomic RNA-containing DI RNA, which is amplified by the nonstructural viral proteins (nsP1-4). This subgenomic RNA contains a translational enhancer, which promotes translation of the heterologous nucleic acid under conditions of virus-induced translational shutoff.

DETAILED DESCRIPTION OF THE INVENTION

Figure 4:
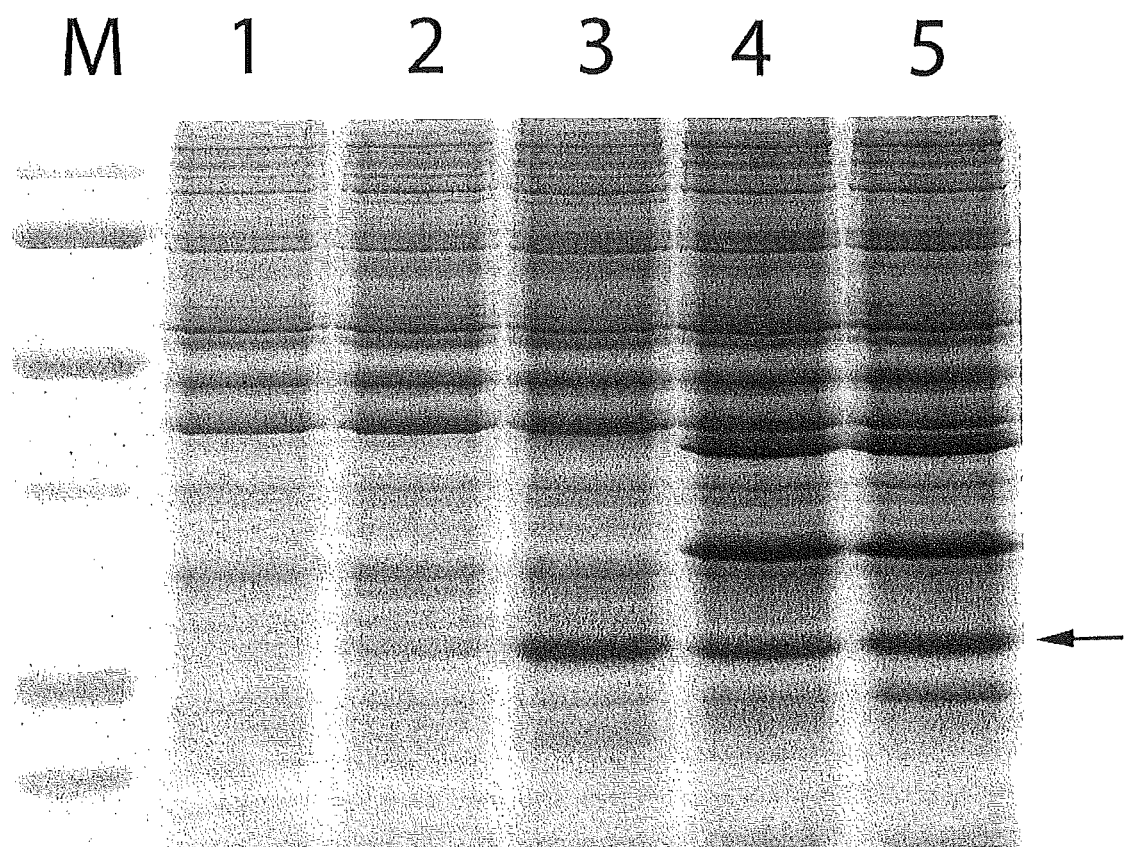
FIG. 4 shows the difference in heterologous protein expression [green fluorescence protein (GFP) expression], indicated by arrow, achieved from the standard Venezuelan equine encephalitis (VEEV) replicon, encoding green fluorescent protein (GFP) in the subgenomic RNA (lane 2) and different VEEV defective interfering (DI) RNA-based constructs (lanes 3-5). Protein accumulation was evaluated at 20 h post infection of BHK-21 cells at a multiplicity of infection (MOI) of 20 infectious units (inf.u) of packaged constructs per cell. Lane 1 represents mock-infected cells. Gel was stained with Coomassie Brilliant Blue. Lane 1 represents a lysate of the uninfected cells. Lane 2 represents the lysate of the cells infected with standard VEEV, GFP-encoding replicon. This standard VEEV replicon contains a 5'UTR of the VEEV genome, followed by nucleic acid sequence encoding alphavirus nonstructural proteins (nsP1-4), a nucleic acid sequence encoding an alphavirus subgenomic promoter, a nucleic acid sequence encoding GFP and a VEEV 3'UTR. Lane 3 represents the lysate from the cells infected with a VEEV, DI RNA-encoding construct comprising a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51 nucleotide conserved sequence element (51-nt CSE); e) a nucleic acid sequence encoding a ubiquitin gene; f) a nucleic acid sequence encoding GFP; and g) a nucleic acid sequence encoding an alphavirus 3' untranslated region (3' UTR). Lane 4 represents a lysate of the cells infected with a VEEV, DI RNA-encoding construct comprising: a) a nucleic acid sequence encoding a first alphavirus 5' untranslated region (5' UTR) and a 51 nucleotide conserved sequence element (51-nt CSE); b) a nucleic acid sequence encoding alphavirus non-structural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51 nucleotide conserved sequence element (51-nt CSE); e) a nucleic acid sequence encoding an FMDV protease; f) a nucleic acid sequence encoding a VEEV capsid gene; g) a nucleic acid sequence encoding GFP; and h) a nucleic acid sequence encoding an alphavirus 3' untranslated region (3' UTR). Lane 5 represents a lysate of the cells infected with a VEEV, DI RNA-encoding construct comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51-nt-CSE; e) a nucleic acid sequence encoding a foot and mouth disease virus (FMDV) protease; f) a nucleic acid sequence encoding a VEEV capsid; g) a nucleic acid sequence encoding ubiquitin; h) a nucleic acid sequence encoding GFP; and i) a nucleic acid sequence encoding an alphavirus 3' untranslated region (3' UTR).
Figure 5:
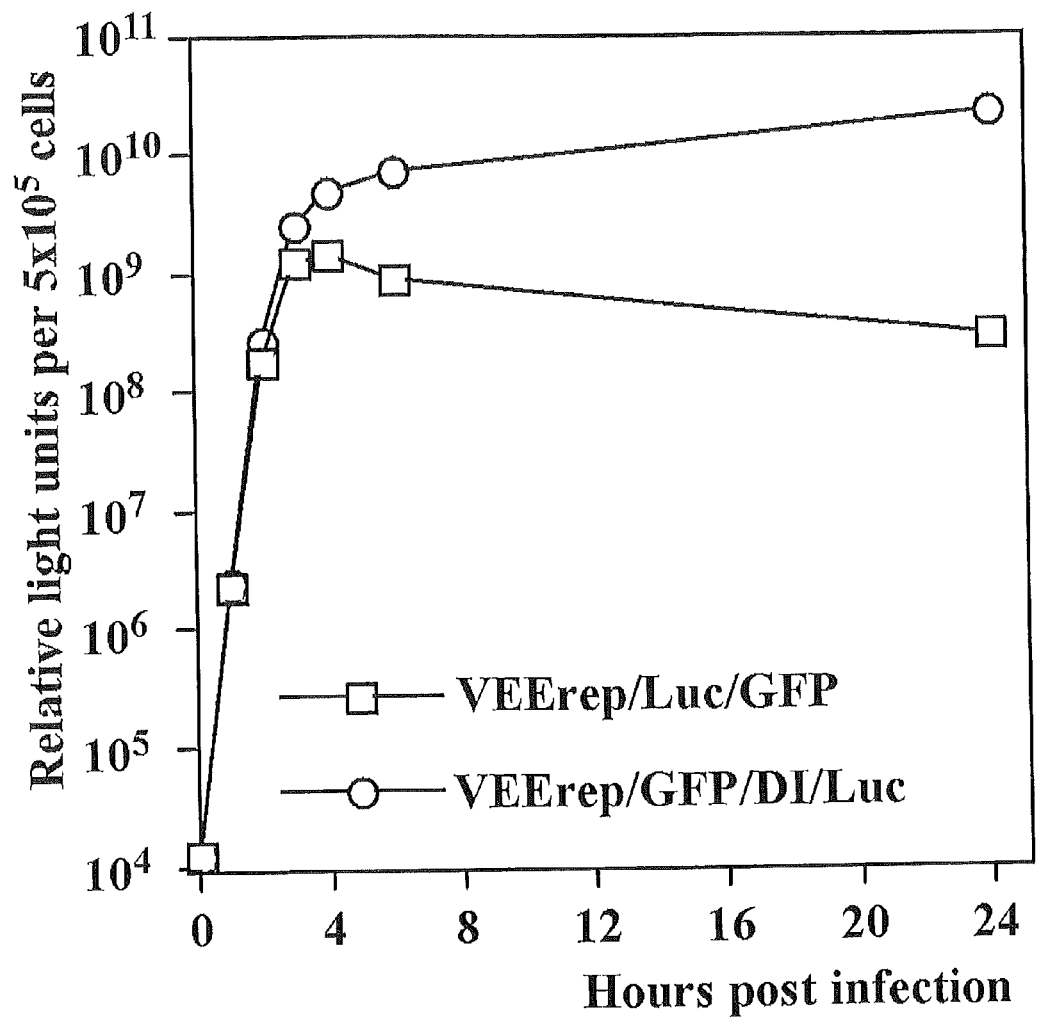
FIG. 5 shows a comparative analysis of luciferase (Luc) expression from a standard VEEV replicon, encoding a luciferase protein under control of the subgenomic promoter and from a replicon encoding amplifiable, luciferase-encoding DI RNA (see FIG. 1). BHK-21 cells were infected at the same MOI with both replicons packaged into viral particles and luciferase activity was measured at different times post infection. The DI RNA-based construct produced 50-100-fold more luciferase. The standard VEEV replicon contained a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding GFP; e) a nucleic acid sequence encoding a second alphavirus subgenomic promoter; 1) a nucleic acid sequence encoding a firefly luciferase gene; g) a nucleic acid sequence encoding an alphavirus 3' untranslated region (3' UTR). VEErep/GFP/DI/Luc replicon contained a) a nucleic acid sequence encoding a first alphavirus 5' untranslated region (5' UTR) and a 51 nucleotide conserved sequence element (51-nt CSE), which represent an essential part of the promoter; b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding GFP; e) a nucleic acid sequence encoding a second alphavirus subgenomic promoter; 1) a nucleic acid sequence encoding a second alphavirus 5' untranslated region (5' UTR) and 51 nucleotide conserved sequence element (51-nt CSE); g) a nucleic acid sequence encoding an FMDV protease; g) a nucleic acid sequence encoding a VEEV capsid; h) a nucleic acid sequence encoding firefly luciferase; and i) a nucleic acid sequence encoding an alphavirus 3' untranslated region (3' UTR).
Figure 6:
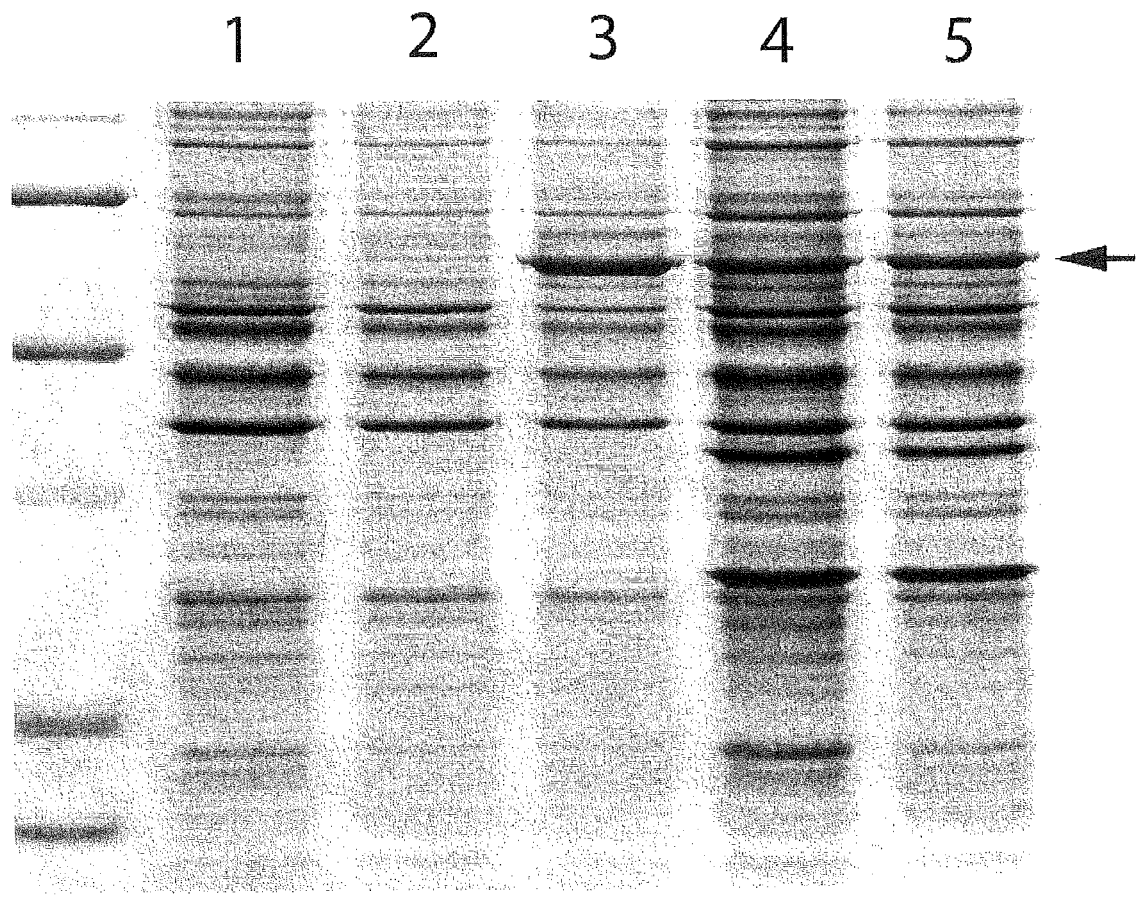
FIG. 6 shows a comparative analysis of luciferase expression achieved from the standard VEEV replicon, encoding Luc in the subgenomic RNA (lane 2) and different VEEV DI RNA-based constructs (lanes 3-5). Lane 1 represents mock-infected cells. Protein production was evaluated at 20 h post infection of BHK-21 cells at a multiplicity of infection (MOI) of 20 infectious units (inf.u) of packaged constructs per cell. Arrow indicates the position of luciferase. Gel was stained with Coomassie Brilliant Blue. Lane 1 represents a lysate of the uninfected cells. Lane 2 represents the lysate of the cells infected with standard VEEV, luciferase-encoding replicon. Standard VEEV replicon contained a) a nucleic acid sequence encoding a first alphavirus 5' untranslated region (5' UTR) and a 51 nucleotide conserved sequence element (51-nt CSE); b) a nucleic acid sequence encoding alphavirus non-structural proteins nsP1, nsP2, nsP3 and nsP4; c) a nucleic acid sequence encoding an alphavirus subgenomic promoter; d) a nucleic acid sequence encoding GFP; e) a nucleic acid sequence encoding a second alphavirus subgenomic promoter; f) a nucleic acid sequence encoding a firefly luciferase gene; g) a nucleic acid sequence encoding an alphavirus 3' untranslated region (3' UTR). Lane 3 represents a lysate of the cells infected with a VEEV, DI RNA-encoding construct containing a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding GFP; e) a nucleic acid sequence encoding a second alphavirus subgenomic promoter; f) a nucleic acid sequence encoding a second alphavirus 5' untranslated region (5' UTR) and 51 nucleotide conserved sequence element (51-nt CSE); g) a nucleic acid sequence encoding a ubiquitin gene; h) a nucleic acid sequence encoding firefly luciferase; and i) a nucleic acid sequence encoding an alphavirus 3' untranslated region (3' UTR). Lane 4 represents a lysate of the cells infected with a VEEV, DI RNA-encoding construct containing a) a nucleic acid sequence encoding a first alphavirus 5' untranslated region (5' UTR) and a 51 nucleotide conserved sequence element (51-nt CSE), which represent an essential part of the promoter; b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding GFP; e) a nucleic acid sequence encoding a second alphavirus subgenomic promoter; f) a nucleic acid sequence encoding a second alphavirus 5' untranslated region (5' UTR) and 51-nt CSE; g) a nucleic acid sequence encoding an FMDV protease; h) a nucleic acid sequence encoding a VEEV capsid; i) a nucleic acid sequence encoding firefly luciferase; and j) a nucleic acid sequence encoding an alphavirus 3' untranslated region (3' UTR). Lane 5 represents a lysate of the cells infected with a VEEV, DI RNA-encoding construct containing a) a nucleic acid sequence encoding a first alphavirus 5' untranslated region (5' UTR) and a 51 nucleotide conserved sequence element (51-nt CSE), which represent an essential part of the promoter; b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding GFP; e) a nucleic acid sequence encoding a second alphavirus subgenomic promoter; f) a nucleic acid sequence encoding a second alphavirus 5' untranslated region (5' UTR) and 51-nt CSE; g) a nucleic acid sequence encoding an FMDV protease; h) a nucleic acid sequence encoding a VEEV capsid; i) a nucleic acid sequence encoding ubiquitin; j) a nucleic acid sequence encoding firefly luciferase; and q) a nucleic acid sequence encoding an alphavirus 3' untranslated region (3' UTR).
Figure 7:
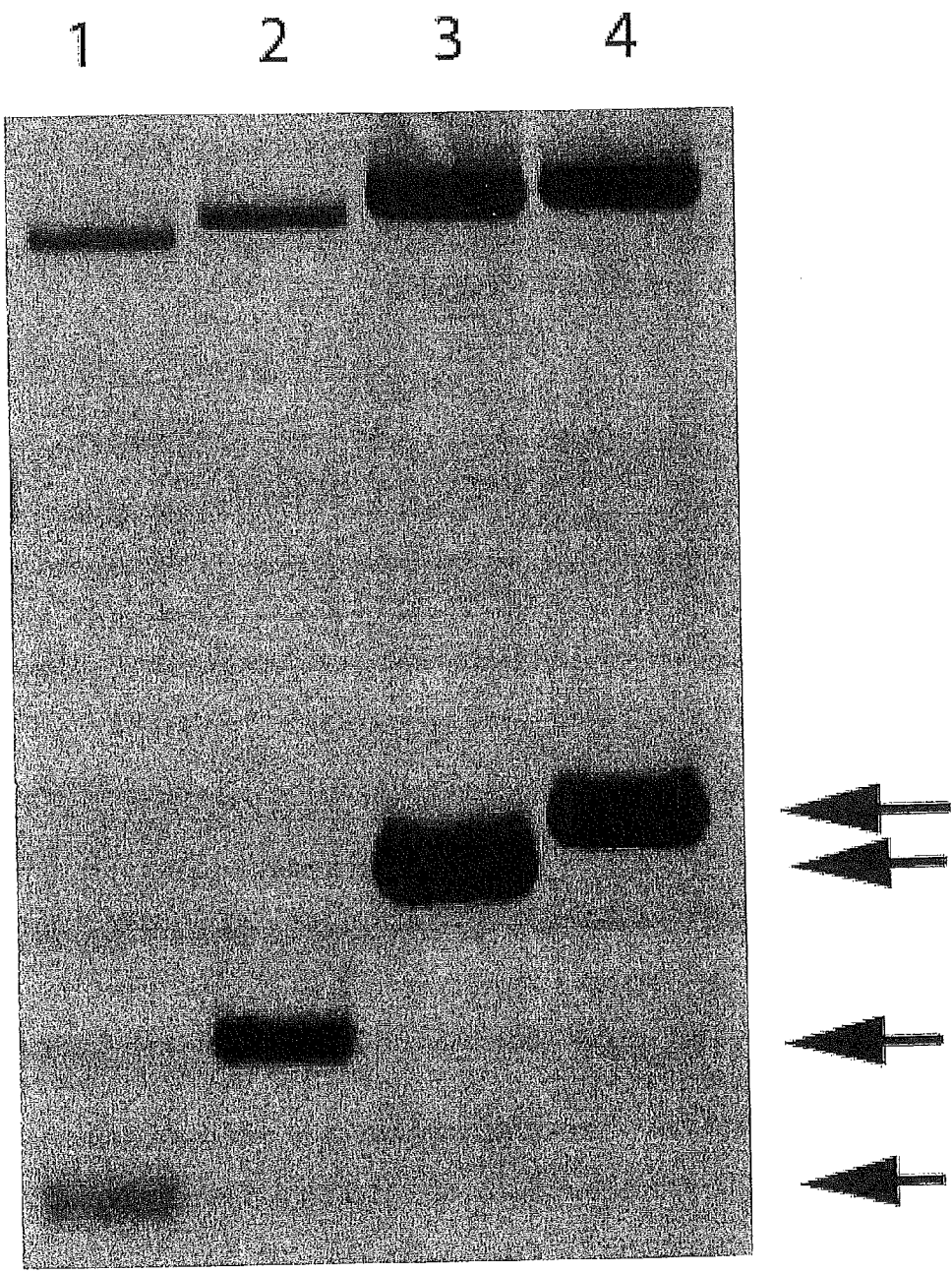
FIG. 7 shows a comparative analysis of synthesis of subgenomic RNAs, encoding heterologous genes, in cells infected with VEEV replicons. Cells were infected with different packaged replicons at a MOI of 20 inf.u/cell and RNAs were metabolically labeled with [$^3$H]uridine in the presence of Actinomycin D (ActD) between 2 and 6 h post infection. Then they were separated by electrophoresis in a 1% agarose gel, dried and exposed to X-ray film. Lane 1 represents an RNA sample isolated from the cells infected with the standard VEEV replicon encoding GFP under control of the subgenomic promoter. Lanes 2-4 represent the samples isolated from the cells infected with replicons encoding GFP in the DI RNA, synthesized from the subgenomic promoter. The latter constructs were designed based on the strategy presented in FIG. 1 and differ in the protease mediating DI RNA-encoded polyprotein cleavage. Lane 1 represents the lysate of the cells infected with standard VEEV, GFP-encoding replicon. This replicon contains a 5'UTR of the VEEV genome, followed by a nucleic acid sequence encoding nonstructural proteins nsP1-4, a nucleic acid sequence encoding a subgenomic promoter, a nucleic acid sequence encoding GFP and a VEEV 3'UTR. Lane 2 represents the lysate from the cells infected with a VEEV, DI RNA-encoding construct containing a) a nucleic acid sequence encoding a first alphavirus 5' untranslated region (5' UTR) and a 51 nucleotide conserved sequence element (51-nt CSE), which represent an essential part of the promoter; b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51 nucleotide conserved sequence element (51-nt CSE); e) a nucleic acid sequence encoding a ubiquitin gene; f) a nucleic acid sequence encoding GFP; and g) a nucleic acid sequence encoding an alphavirus 3' untranslated region (3' UTR). Lane 3 represents a lysate of the cells infected with a VEEV, DI RNA-encoding construct containing a) a nucleic acid sequence encoding a first alphavirus 5' untranslated region (5' UTR) and a 51 nucleotide conserved sequence element (51-nt CSE), which represent an essential part of the promoter; b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51 nucleotide conserved sequence element (51-nt CSE); e) a nucleic acid sequence encoding an FMDV protease; f) a nucleic acid sequence encoding a VEEV capsid gene; g) a nucleic acid sequence encoding GFP; and h) a nucleic acid sequence encoding an alphavirus 3' untranslated region (3' UTR). Lane 4 represents a lysate of the cells infected with a VEEV, DI RNA-encoding construct containing a) a nucleic acid sequence encoding a first alphavirus 5' untranslated region (5' UTR) and a 51 nucleotide conserved sequence element (51-nt CSE), which represent an essential part of the promoter; b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51-nt-CSE; e) a nucleic acid sequence encoding an FMDV protease; f) a nucleic acid sequence encoding a VEEV capsid; g) a nucleic acid sequence encoding ubiquitin; h) a nucleic acid sequence encoding GFP; and i) a nucleic acid sequence encoding an alphavirus 3' untranslated region (3' UTR).

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted.

The present invention is based on the discovery and development of recombinant alphavirus replicons that have enhanced/improved efficiency in protein (e.g., heterologous protein or protein of interest) production, for use, e.g., in immunization (e.g., vaccine) protocols, gene therapy protocols and protein-producing cell systems.

In general, the present invention is directed to the development of a new type of alphavirus genome-based vector, modified for efficient expression of a heterologous nucleotide sequence of interest (NOI). The modified replicon vectors of this invention produce a subgenomic RNA that not only serves as a template for translation of a protein of interest (POI) encoded by the replicon, but also serves as a template for amplification in the presence of viral replication proteins. These additional rounds of amplification of the subgenomic RNA increase the level of intracellular, POI-encoding RNA and consequently increase protein production. This makes the alphavirus replicons of this invention more efficient, for example, in terms of immunogenicity and protein production in eukaryotic cells. The invention takes into consideration differences in the biology of different alphaviruses, and three different strategies of subgenomic RNA amplification and protein production have been developed for broad application in different alphavirus vectors.

Alphavirus replicons (e.g., in alphavirus vectors) are widely applied for example, for expression of heterologous genetic information and for immunization against infection by pathogens (e.g., bacterial and viral pathogens). In an alphavirus replicon, viral structural genes are replaced partially or completely by the genes of interest, and these replicons serve as vectors expressing cloned heterologous genetic information.

The alphavirus replicons of this invention, with amplifiable subgenomic RNAs, produce higher levels of heterologous POIs and can be applied as more efficient immunogens or for more efficient production of POIs. These replicons and constructs comprising them can be used for improvement of i) DNA vaccines, if delivered in DNA form, and ii) RNA vaccines, if delivered as in vitro-synthesized RNA. The replicons of this invention can also be packaged into viral particles and delivered into cells using a natural, virion-mediated route of infection. The replicons of this invention can be applied in a protein production system for the large-scale production of heterologous proteins in eukaryotic cells (e.g., mammalian or insect cells).

Alphaviruses are a group of human and animal pathogens, which are widely distributed all over the world. They replicate in the cytoplasm of the infected cells, and this replication does not depend on nuclei. Alphavirus genomes are represented by single-stranded RNA molecule of positive polarity of almost 11.5 kb. This RNA mimics the structure of cellular messenger RNAs, in that it contains a cap structure at the 5' terminus, and a poly(A) sequence at the 3' terminus. Upon delivery into the cells, the viral genome is translated into the polyprotein precursor of the nonstructural proteins. The latter polyprotein is sequentially self-processed by the encoded protease, and these nonstructural proteins nsP1, nsP2, nsP3 and nsP4 form the replicative enzyme complex, which amplifies the viral genome and synthesizes additional subgenomic RNA that is a template for synthesis of viral structural proteins. These structural proteins (capsid, E2 and E1) ultimately form viral particles.

Characteristics of alphaviruses that are relevant to the development of the recombinant alphavirus replicons of this invention include the following.

1. The alphavirus genome is relatively simple and encodes only seven proteins with only four proteins involved in genome replication. This viral genome can be termed self-amplifying RNA.
2. During virus replication, genetic material of the virus remains in the cytoplasm and cannot integrate into cellular genome.
3. Viral genomes can be manipulated in cDNA form using gene engineering techniques, and then modified genomes can be synthesized in vitro (e.g., by SP6 or T7 DNA-dependent RNA polymerase). If genetic modifications do not affect encoded nonstructural proteins, such RNAs demonstrate self-amplification and produce subgenomic RNAs.
4. In vitro-synthesized, modified genomes can be delivered into cells by numerous transfection techniques or they can be packaged into infectious virus particles. These particles can infect the cells as efficiently as wild type viruses and thus deliver RNA by natural means. Alternatively, alphavirus genomes can be delivered into cells in DNA form under control of promoters recognized by cellular, DNA-dependent RNA polymerase II.
5. Viral structural proteins are encoded by the subgenomic RNA and are not included in the nonstructural polyprotein. They are dispensable for the RNA genome replication/amplification. Structural genes can be deleted or replaced by the heterologous NOI or any other genetic materials.
6. Viral nonstructural proteins, which mediate synthesis of viral genomes and subgenomic RNAs, are overproduced and less than 5% of them are normally involved in RNA synthesis. Thus, nonstructural proteins are strongly underused.
7. The alphavirus genome contains four short promoter elements, which drive RNA synthesis: i) a short 3' sequence adjacent to the poly(A)-tail, which is involved in negative-strand RNA synthesis, ii) the subgenomic promoter, which functions in subgenomic RNA synthesis, iii) the 5' terminus of the viral genome, which encodes a promoter for synthesis of positive-strand viral genomes, and iv) the 51 nucleotide long conserved sequence element (51-nt CSE), which is located in the first 200 5'-terminal nucleotides of the alphaviral genome. This element serves as a strong enhancer of RNA replication.
8. Alphaviruses can form defective interfering (DI) RNAs, which encode no structural or nonstructural proteins, but contain the 5'- and 3'-specific promoters that function in RNA replication.
9. DI RNAs are incapable of self-replication, but utilize the supplied in trans nonstructural proteins to amplify their genomes.

The present invention is based on redesigning of the alphavirus genome to improve protein production. The recombinant replicons of this invention encode a modified subgenomic RNA that is capable of utilizing viral replication enzymes for its own amplification and to serve as a defective interfering (DI) RNA. This amplification results in higher level of accumulation of POI-encoding RNA in cellular cytoplasm and ultimately in a higher level of production of the protein of interest.

Thus, in one aspect, the present invention provides a recombinant replicon nucleic acid comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding an alphavirus subgenomic promoter; d) a nucleic acid sequence encoding a second alphavirus 5' untranslated region (5' UTR) and 51 nucleotide conserved sequence element (51-nt CSE); e) a nucleic acid sequence encoding a protease; f) a nucleic acid sequence encoding a heterologous protein; and g) a nucleic acid sequence encoding an alphavirus 3' untranslated region (3' UTR). In some embodiments of this recombinant replicon nucleic acid, the nucleic acid sequence of (d) can be modified to position all AUGs (start codons) in the nucleic acid sequence into the same open reading frame as the initiating AUG, as would be known to one of skill in the art.

In some embodiments, the recombinant replicon nucleic acid described above can further comprise a nucleic acid sequence encoding an alphavirus capsid protein and at least two amino acids (e.g., 2, 3, 4, 5, 6, 7, 8, 9, 10, etc.) of an alphavirus E3 protein, positioned upstream of the nucleic acid sequence of (f).

In a further aspect, the present invention provides a recombinant replicon nucleic acid comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding a first alphavirus subgenomic promoter; d) a nucleic acid sequence encoding a second alphavirus 5' untranslated region (5' UTR) and a 51 nucleotide conserved sequence element (51-nt CSE); e) a nucleic acid sequence encoding a second alphavirus subgenomic promoter; f) nucleic acid sequence encoding a heterologous protein; and g) a nucleic acid sequence encoding an alphavirus 3' untranslated region (3' UTR).

In an additional aspect, the present invention provides a recombinant replicon nucleic acid comprising: a) a nucleic acid sequence encoding a first alphavirus 5' untranslated region (5' UTR) and a 51 nucleotide conserved sequence element (51-nt CSE); b) a nucleic acid sequence encoding alphavirus nonstructural proteins nsP1, nsP2, nsP3 and nsP4; c) a nucleic acid sequence encoding a first alphavirus subgenomic promoter; d) a nucleic acid sequence encoding a second alphavirus 5' untranslated region (5' UTR) or a modified 5' UTR comprising a cellular Asp tRNA sequence and a 51 nucleotide conserved sequence element (51-nt CSE); e) a nucleic acid sequence encoding a second alphavirus subgenomic promoter; f) a nucleic acid sequence encoding a translational enhancer derived from an Old World alphavirus (e.g., Sindbis, Semliki Forest, Ross River or other Old World alphavirus); g) a nucleic acid sequence encoding a protease; h) a nucleic acid sequence encoding a heterologous protein; and i) a nucleic acid sequence encoding an alphavirus 3' untranslated region (3' UTR).

In various embodiments of the recombinant replicon nucleic acids described above, the protease can be but is not limited to, a 2A protease from foot and mouth disease virus (FMDV), ubiquitin, a ubiquitin-like protein, Npro of pestiviruses and/or an alphavirus capsid-encoded protease.

As used herein, "an alphavirus 5' untranslated region (5' UTR)" means a fragment of the alphavirus genome, which is a natural start of the genomic RNA, located upstream of the initiating AUG of the nsP1 gene.

In addition, as used herein the terms "a conserved sequence element (CSE)" and "a 51 nucleotide conserved sequence element (51-nt CSE)" describe an RNA element that has a similar position, sequence and secondary structure in the genomes of all of the known alphaviruses. It is located in the beginning of the nsP1-coding sequence. The CSE is a part of the promoter involved in the intracellular synthesis of the viral genome.

Also as used herein, "an alphavirus 3' untranslated region (3' UTR)" means the nucleotide sequence located downstream of the termination codon of the E1-coding gene. This sequence is different in different alphaviruses and is virus-specific.

Furthermore, as used herein, "a modified 5' UTR comprising a cellular Asp tRNA sequence" means a sequence of cellular tRNA, which was acquired by some of the naturally occurring defective interfering viral RNAs. This sequence had a strong positive effect on replication of these RNAs.

Also as used herein, "a translational enhancer derived from an Old World alphavirus" means an RNA sequence located about 10-20 nt downstream of the initiating AUG in the subgenomic RNAs in many of the alphaviruses. This sequence is different in all of the alphaviruses, but is always located at the same position and is folded into a stable stem-loop structure. This enhancer can be an artificially designed enhancer that has the same function as a natural one.

As used herein, an "alphavirus subgenomic promoter" or "26S promoter" is a promoter as originally defined in a wild type alphavirus genome that directs transcription of a subgenomic messenger RNA as part of the alphavirus replication process. Such a promoter can have a wild type sequence or a sequence that has been modified from wild type sequence but retains promoter activity.

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention also provides an alphavirus particle comprising a recombinant replicon nucleic acid of this invention. Also provided is a population of infectious, defective, alphavirus particles, comprising, consisting essentially of or consisting of particles comprising an alphavirus replicon nucleic acid of this invention. In some embodiments, the population of this invention has no detectable replication-competent virus, as measured by passage on cell culture and/or other well-known assays for detection of replication competent virus. In some embodiments, the population of this invention has no more than 1 infectious virus particle per $10^5$, $10^6$, $10^7$, $10^8$, or $10^9$ particles, as measured by passage on permissive cells in culture and/or other well known assays for detection of replication competent virus.

In some embodiments of this invention, the nucleic acids and/or the proteins encoded by the nucleic acids of the present invention can comprise attenuating mutations. The phrases "attenuating mutation" and "attenuating amino acid," as used herein, include a nucleotide sequence containing a mutation, or an amino acid encoded by a nucleotide sequence containing a mutation, which results in a decreased probability of causing disease in its host (i.e., reduction in or "attenuation of" virulence), in accordance with standard terminology in the art. See, e.g., Davis et al., MICROBIOLOGY 132 (3d ed. 1980). The phrase "attenuating mutation" excludes mutations or combinations of mutations that would be lethal to the virus. However, it does include those otherwise lethal mutations that can be incorporated in combination with a resuscitating or rescuing mutation that leads to an attenuated phenotype.

Appropriate attenuating mutations will be dependent upon the alphavirus used, and will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of each of which are incorporated herein in their entireties by reference.

Nonlimiting examples of an alphavirus of this invention include eastern equine encephalitis virus (EEEV), Venezuelan equine encephalitis virus (VEEV), western equine encephalitis virus (WEEV), Sindbis virus, South African Arbovirus No. 86 (S.A.AR86), chikungunya virus, o'nyong-nyong virus, Ross River virus, Barmah Forest virus, Everglades, Mucambo, Pixuna, Semliki Forest virus, Middelburg, Getah, Bebaru, Mayaro, Una, Okelbo, Babanki, Fort Morgan, Ndumu, Girwood S.A. virus, Sagiyama virus, Aura virus, Whataroa virus, Kyzlagach virus, Highlands J virus, Buggy Creek virus, and any other virus classified by the International Committee on Taxonomy of Viruses (ICTV) as an alphavirus, as well as subgroups thereof as are known in the art. The complete genomic sequences, as well as the sequences of the various structural and non-structural proteins, are known in the art for numerous alphaviruses and include as nonlimiting examples: Sindbis virus genomic sequence (GenBank® Accession No. J02363, NCBI Accession No. NC_001547), S.A.AR86 genomic sequence (GenBank® Accession No. U38305), VEEV genomic sequence (GenBank® Accession No. L04653, NCBI Accession No. NC_001449), Girdwood S.A genomic sequence (GenBank® Accession No. U38304), Semliki Forest virus genomic sequence GenBank® Accession No. X04129, NCBI Accession No. NC_003215), and the TR339 genomic sequence (Klimstra et al. (1988) *J. Virol.* 72:7357; McKnight et al. (1996) *J. Virol.* 70:1981). These sequences and references are incorporated by reference herein.

The recombinant replicon nucleic acid of this invention can be RNA or DNA. In some embodiments, the replicon nucleic acid can be DNA cloned under the control of SP6, T7 or DNA-dependent RNA polymerase I or II. In some embodiments of this invention, the replicon nucleic acid of this invention can be present in a nucleic acid construct.

In some embodiments of a nucleic acid construct of this invention, a promoter for directing transcription of RNA from DNA, i.e., a DNA dependent RNA polymerase, can be employed. In the RNA replicon nucleic acid embodiments of this invention, the promoter is utilized to synthesize RNA in an in vitro transcription reaction, and specific promoters suitable for this use include, but are not limited to, the SP6, T7, and T3 RNA polymerase promoters. In the DNA replicon nucleic acid embodiments, the promoter functions within a cell to direct transcription of RNA. Potential promoters for in vivo transcription of the construct include, but are not limited to, eukaryotic promoters such as RNA polymerase II promoters, RNA polymerase I and RNA polymerase III promoters, and/or viral promoters such as MMTV and MoSV LTR, SV40 early region, RSV or CMV or β-actin promoter. Many other suitable mammalian and viral promoters for the present invention are available and are known in the art. Alternatively, DNA dependent RNA polymerase promoters from bacteria or bacteriophage, e.g., SP6, T7, and T3, can be employed for use in vivo, with the matching RNA polymerase being provided to the cell, either via a separate plasmid, RNA vector, or viral vector.

In a particular embodiment, the matching RNA polymerase can be stably transformed into a helper cell line under the control of an inducible or continuous promoter. Constructs that function within a cell can function as autonomous plasmids transfected into the cell and/or they can be stably transformed into the genome. In a stably transformed cell line, the promoter can be an inducible promoter, so that the cell will only produce the RNA polymerase encoded by the stably transformed construct when the cell is exposed to the appropriate stimulus (inducer). Helper constructs as described herein are introduced into the stably transformed cell concomitantly with, prior to, and/or after exposure to, the inducer, thereby effecting expression of the alphavirus structural proteins. Alternatively, constructs designed to function within a cell can be introduced into the cell via a viral vector, such as, e.g., adenovirus, poxvirus, adeno-associated virus, SV40, retrovirus, nodavirus, picornavirus, vesicular stomatitis virus, and baculoviruses with mammalian pol II promoters.

The present invention further provides a method of making infectious, defective alphavirus particles, comprising: a) introducing into a cell the following: (i) a recombinant replicon nucleic acid of this invention, and (ii) one or more helper nucleic acids encoding alphavirus structural proteins, wherein the one or more helper nucleic acids produce all of the alphavirus structural proteins, and b) producing said alphavirus particles in the cell. In some embodiments, the recombinant replicon nucleic acid can comprise at least one heterologous nucleic acid encoding an alphavirus structural protein. In some embodiments the replicon nucleic acid contains a packaging signal.

The methods of making alphavirus particles of this invention can further comprise the step of collecting said alphavirus particles from the cell.

The helper nucleic acid of this invention can comprise nucleic acid sequences encoding any one or more of the alphavirus structural proteins (C, E1, E2) in any order and/or in any combination. Thus, a helper cell can comprise as many helper nucleic acids as needed in order to provide all of the alphavirus structural proteins necessary to produce alphavirus particles. A helper cell can also comprise helper nucleic acid(s) stably integrated into the genome of a helper (e.g., packaging) cell. In such helper cells, the alphavirus structural proteins can be produced under the control of a promoter that can be an inducible promoter.

In some embodiments of this invention, a series of helper nucleic acids ("helper constructs" or "helper molecules"), i.e., recombinant DNA or RNA molecules that express one or more alphavirus structural proteins, are provided. In some embodiments, the E1 and E2 glycoproteins are encoded by one helper construct, and the capsid protein is encoded by another separate helper construct. In another embodiment, the E1 glycoprotein, E2 glycoprotein, and capsid protein are each encoded by separate helper constructs. In other embodiments, the capsid protein and one of the glycoproteins are encoded by one helper construct, and the other glycoprotein is encoded by a separate second helper construct. In yet further embodiments, the capsid protein and glycoprotein E1 are encoded by one helper construct and the capsid protein and glycoprotein E2 are encoded by a separate helper construct. In certain embodiments, the helper constructs of this invention do not include an alphavirus packaging signal.

Alternatively, helper nucleic acids can be constructed as DNA molecules, which can be stably integrated into the genome of a helper cell or expressed from an episome (e.g., an EBV derived episome). The DNA molecule can also be transiently expressed in a cell. The DNA molecule can be any vector known in the art, including but not limited to, a non-integrating DNA vector, such as a plasmid, or a viral vector. The DNA molecule can encode one or all of the alphavirus structural proteins, in any combination, as described herein.

The helper constructs of this invention are introduced into "helper cells," which are used to produce the alphavirus particles of this invention. As noted above, the nucleic acids encoding alphavirus structural proteins can be present in the helper cell transiently or by stable integration into the genome of the helper cell. The nucleic acid encoding the alphavirus structural proteins that are used to produce alphavirus particles of this invention can be under the control of constitutive and/or inducible promoters. In particular embodiments, the helper cells of the invention comprise nucleic acid sequences encoding the alphavirus structural proteins in a combination and/or amount sufficient to produce an alphavirus particle of this invention when a recombinant replicon nucleic acid is introduced into the cell under conditions whereby the alphavirus structural proteins are produced and the recombinant replicon nucleic acid is packaged into alphavirus particle of this invention.

The term "alphavirus structural protein/protein(s)" refers to one or a combination of the structural proteins encoded by alphaviruses. These are produced by the wild type virus as a polyprotein and are described generally in the literature as C-E3-E2-6k-E1. E3 and 6k serve as membrane translocation/ transport signals for the two glycoproteins, E2 and E1. Thus, use of the term E1 herein can refer to E1, 6k-E1, or E3-E2- 6k-E1, and use of the term E2 herein can refer to E2, E3-E2, E2-6k, PE2, p62 or E3-E2-6k.

The terms "helper," "helper RNA," "helper molecule," "helper nucleic acid" and "helper construct" are used interchangeably and refer to a nucleic acid molecule (either RNA or DNA) that encodes one or more alphavirus structural proteins. In the present invention, the helper construct generally encodes an RNA-binding competent alphavirus capsid protein. The capsid protein can comprise the amino acid sequence of what is known in the art to be the "wild type" capsid protein of a given alphavirus. Exemplary wild type amino acid sequences of various alphaviruses of this invention are provided herein below. The capsid protein encoded by a helper construct of this invention can also be an alphavirus capsid protein that has the function of binding and packaging alphavirus RNA and may have other modifications that distinguish its amino acid sequence from a wild type sequence, while retaining the RNA binding and packaging function. Optionally, the helper construct of this invention does not comprise a packaging signal. Optionally, the helper construct of this invention can comprise nucleotide sequence encoding all or a portion of one or more alphavirus nonstructural proteins or the helper construct of this invention does not comprise nucleotide sequence encoding all or a portion of one or more alphavirus nonstructural proteins. Further options for the helper construct of this invention can include a helper construct comprising nucleotide sequence encoding all or a portion of one or more alphavirus structural proteins (e.g., in addition to capsid) or the helper construct does not comprise nucleotide sequence encoding one or more alphavirus structural proteins (e.g., besides capsid).

The terms "helper cell" and "packaging cell" are used interchangeably herein and refer to a cell in which alphavirus particles are produced. In particular embodiments, the helper cell or packaging cell of the present invention contains a stably integrated nucleotide sequence encoding an alphavirus RNA-binding competent capsid protein. The helper cell or packaging cell can be any cell that is alphavirus-permissive, i.e., that can produce alphavirus particles upon introduction of an alphavirus genome. Alphavirus-permissive cells of this invention include, but are not limited to, Vero, baby hamster kidney (BHK), 293, 293T/17 (ATCC accession number CRL-11268), chicken embryo fibroblast (CEF), UMNSAH/DF-1 (ATCC accession number CRL-12203) and Chinese hamster ovary (CHO) cells.

An "isolated cell" as used herein is a cell or population of cells that have been removed from the environment in which the cell occurs naturally and/or altered or modified from the state in which the cell occurs in its natural environment. An isolated cell of this invention can be a cell, for example, in a cell culture. An isolated cell of this invention can also be a cell that can be in an animal and/or introduced into an animal and wherein the cell has been altered or modified, e.g., by the introduction into the cell of an alphavirus particle of this invention.

In all of the embodiments of this invention, it is contemplated that at least one of the alphavirus structural and/or non-structural proteins encoded by the recombinant replicon nucleic acid and/or helper molecules, and/or the nontranslated regions of the recombinant replicon and/or helper nucleic acid, can contain one or more attenuating mutations in any combination, as described herein and as are well known in the literature.

The present invention further provides a method of producing a heterologous protein in a cell, comprising introducing a recombinant replicon nucleic acid of this invention and/or an alphavirus particle of this invention into the cell under conditions whereby the heterologous nucleic acid sequence present in the replicon nucleic acid molecule is expressed, thereby producing the heterologous protein in the cell. In some embodiments, the cell can be in a cell culture. In some embodiments, this method further comprises the step of harvesting the heterologous protein from the cell culture. In some embodiments the cell can be in a subject.

In some embodiments, the term "heterologous" as used herein can include a nucleotide sequence that is not naturally occurring in the nucleic acid construct and/or delivery vector (e.g., alphavirus delivery vector) in which it is contained and can also include a nucleotide sequence that is placed into a non-naturally occurring environment and/or non-naturally occurring position relative to other nucleotide sequences (e.g., by association with a promoter or coding sequence with which it is not naturally associated).

In some embodiments, a nucleotide sequence of this invention can encode a protein, peptide and/or RNA of this invention that is heterologous [i.e., not naturally occurring, not present in a naturally occurring state and/or modified and/or duplicated (e.g., in a cell that also produces its own endogenous version of the protein, peptide and/or RNA)] to the cell into which it is introduced. The nucleotide sequence can also be heterologous to the vector (e.g., an alphavirus vector) into which it is placed.

Alternatively, the protein, peptide or RNA (e.g., a heterologous protein, peptide or functional RNA of interest) encoded by the heterologous nucleotide sequence of interest can comprise, consist essentially of, or consist of a nucleotide sequence that may otherwise be endogenous to the cell (i.e., one that occurs naturally in the cell) but is introduced into and/or is present in the cell as an isolated heterologous nucleic acid.

In further embodiments, the present invention provides a method of eliciting an immune response to a heterologous protein in a subject, comprising administering to the subject a recombinant replicon nucleic acid of this invention and/or an alphavirus particle of this invention and/or a composition of this invention comprising a recombinant replicon nucleic acid of this invention and/or an alphavirus particle of this invention, under conditions whereby the heterologous nucleic acid of the recombinant replicon nucleic acid is expressed and the heterologous protein is produced in the subject, thereby eliciting an immune response to the heterologous protein in the subject.

Also provided herein is a method of treating and/or preventing a disease or disorder caused by an alphavirus infection in a subject, comprising administering to the subject a recombinant replicon nucleic acid of this invention, an alphavirus particle of this invention, a population of this invention and/or a pharmaceutical composition of this invention, thereby treating and/or preventing a disease or disorder caused by alphavirus infection in the subject.

Further provided herein is a method of delivering a therapeutic heterologous protein to a subject, comprising administering to the subject a recombinant replicon nucleic acid of this invention, an alphavirus particle of this invention, a population of this invention and/or a pharmaceutical composition of this invention, wherein the heterologous nucleic acid sequence of the replicon nucleic acid encodes a therapeutic protein, under conditions whereby the heterologous nucleic acid of the replicon nucleic acid is expressed and the therapeutic heterologous protein is produced in the subject, thereby delivering a therapeutic heterologous protein to the subject.

A "subject" of this invention includes, but is not limited to, warm-blooded animals, e.g., humans, non-human primates, horses, cows, cats, dogs, pigs, rats, and mice. Administration of the various compositions of this invention (e.g., nucleic acids, particles, populations, pharmaceutical compositions) can be accomplished by any of several different routes. In specific embodiments, the compositions can be administered intramuscularly, subcutaneously, intraperitoneally, intradermally, intranasally, intracranially, sublingually, intravaginally, intrarectally, orally, or topically. The compositions herein may be administered via a skin scarification method, or transdermally via a patch or liquid. The compositions can be delivered subdermally in the form of a biodegradable material that releases the compositions over a period of time.

As used herein, "eliciting an immune response," "enhancing an immune response" and "immunizing a subject" includes the development or enhancement, in a subject, of a humoral and/or a cellular immune response to an alphavirus protein and/or a heterologous protein of this invention (e.g., an immunogen, an antigen, an immunogenic peptide, and/or one or more epitopes). A "humoral" immune response, as this term is well known in the art, refers to an immune response comprising antibodies, while a "cellular" immune response, as this term is well known in the art, refers to an immune response comprising T-lymphocytes and other white blood cells, especially the immunogen-specific response by HLA-restricted cytolytic T-cells, i.e., "CTLs."

An "immunogenic amount" is an amount of the alphavirus particles in the populations of this invention that is sufficient to elicit or enhance an immune response in a subject to which the population of particles is administered or delivered. An amount of from about $10^4$ to about $10^9$, especially $10^6$ to $10^8$, infectious units, or "IU," as determined by assays well known in the art, per dose is considered suitable, depending upon the age and species of the subject being treated. Administration may be by any suitable means, such as intraperitoneally, intramuscularly, intranasally, intravenously, intradermally (e.g., by a gene gun), intrarectally and/or subcutaneously. The compositions herein may be administered via a skin scarification method, and/or transdermally via a patch or liquid. The compositions can be delivered subdermally in the form of a biodegradable material that releases the compositions over a period of time.

As used herein, "effective amount" refers to an amount of a population or composition or formulation of this invention that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, *Remington, The Science And Practice of Pharmacy* (20th ed. 2000)).

As used herein, "eliciting an immune response" and "immunizing a subject" includes the development, in a subject, of a humoral and/or a cellular immune response to a protein or polypeptide of this invention (e.g., an immunogen, an antigen, an immunogenic peptide, and/or one or more epitopes). A "humoral" immune response, as this term is well known in the art, refers to an immune response comprising antibodies, while a "cellular" immune response, as this term is well known in the art, refers to an immune response comprising T-lymphocytes and other white blood cells, especially the immunogen-specific response by HLA-restricted cytolytic T-cells, i.e., "CTLs." A cellular immune response occurs when the processed immunogens, i.e., peptide fragments, are displayed in conjunction with the major histocompatibility complex (MHC) HLA proteins, which are of two general types, class I and class II. Class I HLA-restricted CTLs generally bind 9-mer peptides and present those peptides on the cell surface. These peptide fragments in the context of the HLA Class I molecule are recognized by specific T-Cell Receptor (TCR) proteins on T-lymphocytes, resulting in the activation of the T-cell. The activation can result in a number of functional outcomes including, but not limited to expansion of the specific T-cell subset resulting in destruction of the cell bearing the HLA-peptide complex directly through cytotoxic or apoptotic events or the activation of non-destructive mechanisms, e.g., the production of interferon/cytokines. Presentation of immunogens via Class I MHC proteins typically stimulates a CD8+ CTL response.

Another aspect of the cellular immune response involves the HLA Class II-restricted T-cell responses, involving the activation of helper T-cells, which stimulate and focus the activity of nonspecific effector cells against cells displaying the peptide fragments in association with the MHC molecules on their surface. At least two types of helper cells are recognized: T-helper 1 cells (Th1), which secrete the cytokines interleukin 2 (IL-2) and interferon-gamma and T-helper 2 cells (Th2), which secrete the cytokines interleukin 4 (IL-4), interleukin 5 (IL-5), interleukin 6 (IL-6) and interleukin 10 (IL-10). Presentation of immunogens via Class II MHC proteins typically elicits a CD4+ CTL response as well as stimulation of B lymphocytes, which leads to an antibody response.

An "immunogenic polypeptide," "immunogenic peptide," or "immunogen" as used herein includes any peptide, protein or polypeptide that elicits an immune response in a subject and in certain embodiments, the immunogenic polypeptide is suitable for providing some degree of protection to a subject against a disease. These terms can be used interchangeably with the term "antigen."

In certain embodiments, the immunogen of this invention can comprise, consist essentially of, or consist of one or more "epitopes." An "epitope" is a set of amino acid residues that is involved in recognition by a particular immunoglobulin. In the context of T cells, an epitope is defined as the set of amino acid residues necessary for recognition by T cell receptor proteins and/or MHC receptors. In an immune system setting, in vivo or in vitro, an epitope refers to the collective features of a molecule, such as primary, secondary and/or tertiary peptide structure, and/or charge, that together form a site recognized by an immunoglobulin, T cell receptor and/or HLA molecule. In the case of a B-cell (antibody) epitope, it is typically a minimum of 3-4 amino acids, preferably at least 5, ranging up to approximately 50 amino acids. Preferably, the humoral response-inducing epitopes are between 5 and 30 amino acids, usually between 12 and 25 amino acids, and most commonly between 15 and 20 amino acids. In the case of a T-cell epitope, an epitope includes at least about 7-9 amino acids, and for a helper T-cell epitope, at least about 12-20 amino acids. Typically, such a T-cell epitope will include between about 7 and 15 amino acids, e.g., 7, 8, 9, 10, 11, 12, 13, 14 or 15 amino acids.

The present invention can be employed to express a nucleic acid encoding an immunogenic polypeptide in a subject (e.g., for vaccination) or for immunotherapy (e.g., to treat a subject with cancer or tumors). Thus, in the case of vaccines, the present invention thereby provides methods of eliciting an immune response in a subject, comprising administering to the subject an immunogenic amount of a nucleic acid, particle, population and/or composition of this invention.

It is also contemplated that the nucleic acids, particles, populations and pharmaceutical compositions of this invention can be employed in methods of delivering a NOI of interest to a cell, which can be a cell in a subject. Thus, the present invention provides a method of delivering a heterologous nucleic acid to a cell comprising introducing into a cell an effective amount of a nucleic acid, particle, population and/or composition of this invention. Also provided is a method of delivering a heterologous nucleic acid to a cell in a subject, comprising delivering to the subject an effective amount of a nucleic acid, particle, population and/or composition of this invention. Such methods can be employed to impart a therapeutic effect on a cell and/or a subject of this invention, according to well known protocols for gene therapy.

In some embodiments, the heterologous nucleic acid of this invention can encode a protein or peptide and in some embodiments the heterologous nucleic acid of this invention can encode a functional RNA, as is well known in the art.

The heterologous nucleic acid of this invention can encode a protein or peptide, which can be, but is not limited to, an antigen, an immunogen or immunogenic polypeptide or peptide, a fusion protein, a fusion peptide, a cancer antigen, etc. Examples of proteins and/or peptides encoded by the heterologous nucleic acid of this invention include, but are not limited to, immunogenic polypeptides and peptides suitable for protecting a subject against a disease, including but not limited to microbial, bacterial, protozoal, parasitic, and viral diseases.

In some embodiments, for example, the protein or peptide encoded by the heterologous nucleic acid can be an orthomyxovirus immunogen (e.g., an influenza virus protein or peptide such as the influenza virus hemagglutinin (HA) surface protein or the influenza virus nucleoprotein, or an equine influenza virus protein or peptide), or a parainfluenza virus immunogen, or a metapneumovirus immunogen, or a respiratory syncytial virus immunogen, or a rhinovirus immunogen, a lentivirus immunogen (e.g., an equine infectious anemia virus protein or peptide, a Simian Immunodeficiency Virus (SIV) protein or peptide, or a Human Immunodeficiency Virus (HIV) protein or peptide, such as the HIV or SIV envelope GP160 protein, the HIV or SIV matrix/capsid proteins, and the HIV or SIV gag, pol and env gene products). The protein or peptide can also be an arenavirus immunogen (e.g., Lassa fever virus protein or peptide, such as the Lassa fever virus nucleocapsid protein and the Lassa fever envelope glycoprotein), a picornavirus immunogen (e.g., a Foot and Mouth Disease virus protein or peptide), a poxvirus immunogen (e.g., a vaccinia protein or peptide, such as the vaccinia L1 or L8 protein), an orbivirus immunogen (e.g., an African horse sickness virus protein or peptide), a flavivirus immunogen (e.g., a yellow fever virus protein or peptide, a West Nile virus protein or peptide, or a Japanese encephalitis virus protein or peptide), a filovirus immunogen (e.g., an Ebola virus protein or peptide, or a Marburg virus protein or peptide, such as NP and GP proteins), a bunyavirus immunogen (e.g., RVFV, CCHF, and SFS proteins or peptides), or a coronavirus immunogen (e.g., an infectious human coronavirus protein or peptide, such as the human coronavirus envelope glycoprotein, or a porcine transmissible gastroenteritis virus protein or peptide, or an avian infectious bronchitis virus protein or peptide). The protein or polypeptide encoded by the heterologous nucleic acid of this invention can further be a polio antigen, herpes antigen (e.g., CMV, EBV, HSV antigens) mumps antigen, measles antigen, rubella antigen, varicella antigen, botulinum toxin, diphtheria toxin or other diphtheria antigen, pertussis antigen, hepatitis (e.g., Hepatitis A, Hepatitis B, Hepatitis C, Hepatitis D, or Hepatitis E) antigen, or any other vaccine antigen known in the art.

The compositions of this invention can be used prophylactically to prevent disease or therapeutically to treat disease. Diseases that can be treated include infectious disease caused by viruses, bacteria, fungi or parasites, and cancer. Chronic diseases involving the expression of aberrant or abnormal proteins or the over-expression of normal proteins, can also be treated, e.g., Alzheimer's, disease multiple sclerosis, stroke, etc.

The replicons, particles and/or compositions of this invention can be optimized and combined with other vaccination regimens to provide the broadest (i.e., all aspects of the immune response, including those features described herein) cellular and humoral responses possible. In certain embodiments, this can include the use of heterologous prime-boost strategies, in which the compositions of this invention are used in combination with a composition comprising one or more of the following: immunogens derived from a pathogen or tumor, recombinant immunogens, naked nucleic acids, nucleic acids formulated with lipid-containing moieties, non-alphavirus vectors (including but not limited to pox vectors, adenoviral vectors, herpes vectors, vesicular stomatitis virus vectors, paramyxoviral vectors, parvovirus vectors, papovavirus vectors, retroviral vectors), and other alphavirus vectors. The viral vectors can be virus-like particles or nucleic acids. The alphavirus vectors can be replicon-containing particles, DNA-based replicon-containing vectors (sometimes referred to as an "ELVIS" system, see, for example, U.S. Pat. No. 5,814,482) or naked RNA vectors.

The compositions of the present invention can also be employed to produce an immune response against chronic or latent infectious agents, which typically persist because they fail to elicit a strong immune response in the subject. Illustrative latent or chronic infectious agents include, but are not limited to, hepatitis B, hepatitis C, Epstein-Barr Virus, herpes viruses, human immunodeficiency virus, and human papilloma viruses. Alphavirus vectors encoding peptides and/or proteins from these infectious agents can be administered to a cell or a subject according to the methods described herein.

Alternatively, the immunogenic protein or peptide can be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S. A. Rosenberg, (1999) Immunity 10:281) and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl (asparaginyl) β-hydroxylase (HAAH), and EphA2 (an epithelial cell tyrosine kinase, see International Patent Publication No. WO 01/12172).

The immunogenic polypeptide or peptide of this invention can also be a "universal" or "artificial" cancer or tumor cell antigen as described in international patent publication WO 99/51263, which is incorporated herein by reference in its entirety for the teachings of such antigens.

In various embodiments, the heterologous nucleic acid of this invention can encode an antisense nucleic acid sequence. An "antisense" nucleic acid is a nucleic acid molecule (i.e., DNA or RNA) that is complementary (i.e., able to hybridize in vivo or under stringent in vitro conditions) to all or a portion of a nucleic acid (e.g., a gene, a cDNA and/or mRNA) that encodes or is involved in the expression of nucleic acid that encodes a polypeptide to be targeted for inhibited or reduced production by the action of the antisense nucleic acid. If desired, conventional methods can be used to produce an antisense nucleic acid that contains desirable modifications. For example, a phosphorothioate oligonucleotide can be used as the antisense nucleic acid to inhibit degradation of the antisense oligonucleotide by nucleases in vivo. Where the antisense nucleic acid is complementary to a portion of the nucleic acid encoding the polypeptide to be targeted, the antisense nucleic acid should hybridize close enough to the 5' end of the nucleic acid encoding the polypeptide such that it inhibits translation of a functional polypeptide. Typically, this means that the antisense nucleic acid should be complementary to a sequence that is within the 5' half or third of the nucleic acid to which it hybridizes.

An antisense nucleic acid of this invention can also encode a catalytic RNA (i.e., a ribozyme) that inhibits expression of a target nucleic acid in a cell by hydrolyzing an mRNA encoding the targeted gene product. Additionally, hammerhead RNA can be used as an antisense nucleic acid to prevent intron splicing. An antisense nucleic acid of this invention can be produced and tested according to protocols routine in the art for antisense technology.

The present invention further provides a composition (e.g., a pharmaceutical composition) comprising a replicon nucleic acid, a nucleic acid vector, a virus particle and/or a population of alphavirus particles of this invention in a pharmaceutically acceptable carrier.

By "pharmaceutically acceptable" is meant a material that is not biologically or otherwise undesirable, i.e., the material may be administered to a subject along with the selected particles, and/or populations thereof, without causing substantial deleterious biological effects or interacting in a deleterious manner with any of the other components of the composition in which it is contained. The pharmaceutically acceptable carrier is suitable for administration or delivery to humans and other subjects of this invention. The carrier would naturally be selected to minimize any degradation of the active ingredient and to minimize any adverse side effects in the subject, as would be well known to one of skill in the art (see, e.g., *Remington's Pharmaceutical Science*; latest edition). Pharmaceutical formulations, such as vaccines or other immunogenic compositions of the present invention can comprise an immunogenic amount of the alphavirus particles of this invention, in combination with a pharmaceutically acceptable carrier. Exemplary pharmaceutically acceptable carriers include, but are not limited to, sterile pyrogen-free water and sterile pyrogen-free physiological saline solution.

Furthermore, any of the compositions of this invention can comprise a pharmaceutically acceptable carrier and a suitable adjuvant. As used herein, "suitable adjuvant" describes an adjuvant capable of being combined with the peptide or polypeptide of this invention to further enhance an immune response without deleterious effect on the subject or the cell of the subject. A suitable adjuvant can be, but is not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), aluminum salts (alum), aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion. Adjuvants can be combined, either with the compositions of this invention or with other vaccine compositions that can be used in combination with the compositions of this invention. Examples of adjuvants can also include, but are not limited to, oil-in-water emulsion formulations, immunostimulating agents, such as bacterial cell wall components or synthetic molecules, or oligonucleotides (e.g. CpGs) and nucleic acid polymers (both double stranded and single stranded RNA and DNA), which can incorporate alternative backbone moieties, e.g., polyvinyl polymers.

The compositions of the present invention can also include other medicinal agents, pharmaceutical agents, carriers, diluents, immunostimulatory cytokines, etc. Actual methods of preparing such dosage forms are known, or will be apparent, to those skilled in this art. Preferred dosages for alphavirus replicon particles, as contemplated by this invention, can range from $10^3$ to $10^{10}$ particles per dose. For humans, $10^6$, $10^7$ or $10^8$ are preferred doses. A dosage regimen can be one or more doses hourly, daily, weekly, monthly, yearly, etc. as deemed necessary to achieve the desired prophylactic and/or therapeutic effect to be achieved by administration of a composition of this invention to a subject. The efficacy of a particular dosage can be determined according to methods well known in the art.

Alternatively, pharmaceutical formulations of the present invention may be suitable for administration to the mucous membranes of a subject (e.g., via intranasal administration, buccal administration and/or inhalation). The formulations may be conveniently prepared in unit dosage form and may be prepared by any of the methods well known in the art.

Also, the composition of this invention may be used to infect or be transfected into dendritic cells, which are isolated or grown from a subject's cells, according to methods well known in the art, or onto bulk peripheral blood mononuclear cells (PBMC) or various cell subfractions thereof from a subject.

If ex vivo methods are employed, cells or tissues can be removed and maintained outside the body according to standard protocols well known in the art while the compositions of this invention are introduced into the cells or tissues.

Immunogenic compositions comprising a population of the particles of the present invention may be formulated by any means known in the art. Such compositions, especially vaccines, are typically prepared as injectables, either as liquid solutions or suspensions. Solid forms suitable for solution in, or suspension in, liquid prior to injection may also be prepared. Lyophilized preparations are also suitable.

The active immunogenic ingredients (e.g., the virus particles) are often mixed with excipients and/or carriers that are pharmaceutically acceptable and/or compatible with the active ingredient. Suitable excipients include but are not limited to sterile water, saline, dextrose, glycerol, ethanol, or the like and combinations thereof, as well as stabilizers, e.g., HSA or other suitable proteins and reducing sugars.

In addition, if desired, the vaccines or immunogenic compositions may contain minor amounts of auxiliary substances such as wetting and/or emulsifying agents, pH buffering agents, and/or adjuvants that enhance the effectiveness of the vaccine or immunogenic composition. Examples of adjuvants which may be effective include but are not limited to: QS-21, Freund's adjuvant (complete and incomplete), aluminum salts (alum), aluminum phosphate, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion.

Additional examples of adjuvants can include, but are not limited to, immunostimulating agents, such as bacterial cell wall components or synthetic molecules, or oligonucleotides (e.g., CpGs) and nucleic acid polymers (both double stranded and single stranded RNA and DNA), which can incorporate alternative backbone moieties, e.g., polyvinyl polymers.

The effectiveness of an adjuvant may be determined by measuring the amount of antibodies or cytotoxic T-cells directed against the immunogenic product of the alphavirus particles resulting from administration of the particle-containing composition in a vaccine formulation that also comprises an adjuvant or combination of adjuvants. Such additional formulations and modes of administration as are known in the art may also be used.

Adjuvants can be combined, either with the compositions of this invention or with other vaccine formulations that can be used in combination with the compositions of this invention.

The compositions of the present invention can also include other medicinal agents, pharmaceutical agents, carriers, and diluents.

The compositions of this invention can be optimized and combined with other vaccination regimens to provide the broadest (i.e., covering all aspects of the immune response, including those features described hereinabove) cellular and humoral responses possible. In certain embodiments, this can include the use of heterologous prime-boost strategies, in which the compositions of this invention are used in combination with a composition comprising one or more of the following: immunogens derived from a pathogen or tumor, recombinant immunogens, naked nucleic acids, nucleic acids formulated with lipid-containing moieties, non-alphavirus vectors (including but not limited to pox vectors, adenoviral vectors, adeno-associated viral vectors, herpes virus vectors, vesicular stomatitis virus vectors, paramyxoviral vectors, parvovirus vectors, papovavirus vectors, retroviral vectors, lentivirus vectors), and other alphavirus vectors.

The immunogenic (or otherwise biologically active) alphavirus particle-containing populations and compositions of this invention are administered in a manner compatible with the dosage formulation, and in such amount as will be prophylactically and/or therapeutically effective. The quantity to be administered, which can generally be in the range of about $10^4$ to about $10^{10}$ infectious units in a dose (e.g., about $10^4$, about $10^5$, about $10^6$, about $10^7$, about $10^8$, about $10^9$, or about $10^{10}$), depends on the subject to be treated, the route by which the particles are administered or delivered, the immunogenicity of the expression product, the types of effector immune responses desired, and the degree of protection desired. In some embodiments, doses of about $10^6$, about $10^7$, and about $10^8$ infectious units may be particularly effective in human subjects. Effective amounts of the active ingredient required to be administered or delivered may depend on the judgment of the physician, veterinarian or other health practitioner and may be specific for a given subject, but such a determination is within the skill of such a practitioner.

The compositions and formulations of this invention may be given in a single dose or multiple dose schedule. A multiple dose schedule is one in which a primary course of administration may include 1 to 10 or more separate doses, followed by other doses administered at subsequent time intervals as required to maintain and or reinforce the desired effect (e.g., an immune response), e.g., weekly or at 1 to 4 months for a second dose, and if needed, a subsequent dose(s) after several months (e.g., 4 or 6 months)/years.

Efficacy of the treatment methods of this invention can be determined according to well known protocols for determining the outcome of a treatment of a disease or infection of this invention. Determinants of efficacy of treatment, include, but are not limited to, overall survival, disease-free survival, improvement in symptoms, time to progression and/or quality of life, etc., as are well known in the art.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, delay of the onset of the disorder, disease or illness, and/or change in any of the clinical parameters of a disorder, disease or illness, etc., as would be well known in the art.

The terms "preventing" or "prevent" as used herein refers to the prophylactic administration of the alphavirus particles of this invention to a subject to protect the subject from becoming infected by the alphavirus and/or to reduce the severity of an alphavirus infection in a subject who becomes infected. Such as subject can be a healthy subject for whom prevention of infection by an alphavirus is desirable. The subject can also be at increased risk of becoming infected by an alphavirus and therefore desires and/or is in need of the methods of preventing alphavirus infection provided herein.

It is understood that the foregoing detailed description is given merely by way of illustration and that modifications and variations may be made therein without departing from the spirit and scope of the invention.

EXAMPLES

Alphaviruses strongly differ in their biology and interaction with the host. Therefore, in order to apply the same defective interfering (DI) RNA-based technology of this invention to a wide variety of alphavirus vectors, three different strategies of vector/replicon design were developed.

The rationale used in this invention is to utilize the above-described, natural characteristics of alphavirus RNA replication for high-level production of heterologous proteins of interest (and in some embodiments, functional RNAs of interest). To achieve this, the recombinant genomes of this invention combine sequences encoding both the replicative enzymes and DI RNAs, which are capable of efficient utilization of these enzymes. In studies described herein, application of modified expression vectors unambiguously demonstrated 7-50 fold higher efficiency in terms of protein production, compared to standard, widely used alphavirus replicon-based vectors.

A) Venezuelan equine encephalitis virus (VEEV)-based constructs (FIG. 1) encode nonstructural proteins and promoter elements derived from VEEV TC-83 or other VEEV strains. However, the subgenomic RNA, which is located under control of the subgenomic promoter, is very different. Instead of its natural 5' untranslated region (5'UTR), it encodes a 5'UTR of the viral genome, followed by the RNA fragment, containing the 51-nt CSE. All together, the 5'UTR and following genome sequence are 225-nt-long. In some embodiments, a few (e.g., 1, 2, 3, 4, 5, 6, 7, 8, 9, 10, etc.) nucleotide deletions can be made to position all of the AUGs in the sequence into the same open reading (ORF) with the standard initiating AUG. None of the mutations affect putative RNA secondary structure, which determines the function of the RNA promoter and following enhancer. The described sequence is followed by a nucleotide sequence encoding a protease (e.g., 2A protease derived from foot and mouse disease virus (FMDV), and a nucleotide sequence encoding one or more proteins of interest, also cloned in frame with the upstream sequence. The 3'UTR is standard for the VEEV genome. The protease (e.g., FMDV-2A) is included only for polyprotein processing and other proteins can be used, such as ubiquitin, alphavirus capsid protein or any other protease that mediates the same proteolytic cleavage function.

Upon delivery of such a replicon RNA into the cell, the sequence of events is as follows:

1. Recombinant RNA genome serves as a template for synthesis of viral nonstructural proteins.
2. The nonstructural proteins produce the negative strand of the viral genome in the form of a double-stranded RNA intermediate. It serves for synthesis of new copies of viral genome, which are the templates for new nonstructural proteins and, thus, amplification starts. This process is disproportionate and the amount of synthesized viral nonstructural proteins (the RNA-synthesizing protein complexes) is higher than the number of the RNA-containing complexes, which actually perform the RNA synthesis.
3. Besides viral genomes, the nonstructural proteins synthesize viral subgenomic RNA. In contrast to the natural counterpart, this subgenomic RNA contains all of the RNA promoter elements. Thus, it can utilize viral nonstructural proteins for its own amplification, and this amplification results in accumulation of the protein of interest-coding RNA to high level.
4. Replication of VEEV-specific RNAs and accumulation of the nonstructural proteins does not induce translational shutoff, which is a characteristic feature of replication of the Old World alphavirus, such as Sindbis, chikungunya and Semliki Forest virus. Therefore, the amplified subgenomic RNAs, encoded by the modified VEEV genome, do not require any additional structural features for efficient translation. Their presence at high concentration leads to efficient translation of the encoded protein of interest and ultimately to high-level accumulation of this protein.

B) A different modification of a New World alphavirus, a DI RNA encoding replicon, is shown in FIG. 2. The subgenomic, DI genome-encoding RNA in the modified genome is also located under control of the subgenomic promoter. Instead of the natural 5'UTR, it encodes the 5'UTR of the viral genome, followed by an RNA fragment containing the 51-nt CSE. All together, the 5'UTR and following nucleotide sequence are more than 225-nt-long. This sequence is followed by the standard promoter of the subgenomic RNA, the sequence encoding heterologous gene of interest and virus-specific 3'UTR.

The distinguishing feature of this design is that the DI RNA cloned under control of the subgenomic promoter has an additional subgenomic RNA of its own. After synthesis of the DI genome from the subgenomic promoter, it is not only amplified by viral nonstructural proteins, but serves also as a template for efficient synthesis of subgenomic RNA, which is a template for translation of the encoded heterologous protein of interest. Thus, this alternative design leads to the same result: efficient amplification of the subgenomic, DI RNA-like RNA, encoding the protein of interest, by viral replicative machinery and efficient production of the latter protein.

C) The New World alphaviruses (such as VEEV) are not the only ones used for delivery and expression of heterologous genes. The Old World alphaviruses, such as Sindbis virus and Semliki Forest virus, are also widely applied as expression vectors. They have attracted wide attention because of their better safety records; however, they demonstrate an important difference in comparison with the above-described New World alphavirus-based expression systems. Sindbis and Semliki Forest viruses induce profound translational shutoff within a few hours post infection. This inhibition of translation has a strong negative effect on translation of cellular mRNAs. However, in these conditions, viral subgenomic, but not genomic RNA remains efficiently translated due to the presence of a particular structural and sequence element, termed the translation enhancer, in the beginning of the coding sequence. This translation enhancer cannot be cloned into the beginning of the DI RNA sequence, because its presence destroys the function of the newly cloned 51-nt CSE, which is required for DI/subgenomic RNA replication. Thus, the genome design presented in FIG. 1 is applicable to the New World alphaviruses, but not to those isolated in the Old World.

The strategy presented in FIG. 2 is generally applicable to Sindbis- and Semliki Forest virus-based vectors, but needs an additional modification (see FIG. 3 for details). In the modified genome, the subgenomic, DI RNA genome-encoding RNA is also located under control of the subgenomic promoter, Instead of a natural 5'UTR, it encodes a 5'UTR of either the viral genome or its modified version, derived from the naturally occurring DI RNA, which contains a modified cellular Asp tRNA sequence, followed by the RNA fragment, containing the 51-nt CSE. The indicated tRNA sequence has been found in some of the naturally occurring DI RNAs. All together, the 5'UTR and the following genome sequence are more than 250-nt-long. This sequence is followed by i) the standard promoter of the subgenomic RNA, ii) the subgenomic RNA-specific 5'UTR, and iii) the beginning of the capsid-coding sequence, which contains a translational enhancer. The latter sequence is fused in frame with a nucleotide sequence encoding a protease (e.g., FMDV-2A protease) and heterologous nucleotide sequence of interest followed by the virus-specific 3'UTR. In some embodiments, the enhancer and protease coding sequence can be replaced by the entire capsid coding sequence. In some embodiment, the protease can be ubiquitin or Npro of pestiviruses.

Replication of this recombinant genome leads to synthesis of the subgenomic, DI RNA, followed by its amplification and production of the DI RNA-encoded, subgenomic RNA. The latter RNA has a translational enhancer, located upstream of the heterologous nucleic acid sequence of interest and thus, is translated very efficiently in spite of development of translational shutoff.

In summary, this strategy of gene expression is based on amplification of vector-encoded DI RNA, containing in its genome at least one subgenomic RNA. This subgenomic RNA encodes a translational enhancer, which allows RNA translation to take place in the conditions of profound, virus-induced translational shutoff. Taken together, the above-described modifications strongly increase expression of heterologous nucleotide sequences of interest, compared to standard, commonly used Sindbis- and Semliki Forest virus-based vectors.

The above described strategies of heterologous gene expression can be applied to DNA-based vectors. The described DI RNA-encoding replicons can be cloned into plasmids under control of RNA Pol II promoters. Upon delivery into the cells, the first copies of the replicon RNAs are produced by RNA pol II and then production of the replicon RNAs continues via self replication and amplification of the DI RNA, which encodes the heterologous nucleic acid of interest.

Alphaviruses are attracting more and more attention as gene delivery and expression vectors. This growing interest is based on their user-friendly characteristics, such as simple means of modification of their genomes in DNA form and then efficient production of infectious genomes in vitro. These genomes represent so-called self-replicating RNAs. Within a few hours after their delivery into cells, such self-replicating RNAs can produce heterologous protein products, and these proteins can be produced at high levels. However, the natural design of the alphavirus-based vectors can be additionally modified according to the present invention to achieve even higher levels of heterologous protein production. This makes them more efficient expression vectors in terms of protein production and more efficient recombinant vaccines. Alphavirus-based expression vectors are used, for example, for development of new generations of vaccines against dengue viruses, West Nile virus, TBEV, HCV, HIV, rabies virus, RSV, etc. By employing the replicon nucleic acids of this invention, the efficiency of these vaccine candidates can be greatly increased by more efficient protein production.

The invention is also directed to a method of large-scale, inexpensive protein production in eukaryotic cells.

As will be understood by one skilled in the art, there are several embodiments and elements for each aspect of the claimed invention, and all combinations of different elements are incorporated herein as embodiments of this invention, so the specific combinations exemplified herein are not to be construed as limitations in the scope of the invention as claimed. If specific elements are removed or added to the group of elements available in a combination, then the group of elements is to be construed as having incorporated such a change.

All references cited herein, including non-patent publications, patent applications, GenBank® Database accession numbers and patents, are incorporated by reference herein in their entireties to the same extent as if each was individually and specifically indicated to be incorporated by reference, and was reproduced in its entirety herein.

What is claimed is:

1. A recombinant replicon nucleic acid comprising:
   a) a nucleic acid sequence encoding a first alphavirus 5' untranslated region (5' UTR) and a 51 nucleotide conserved sequence element (51-nt CSE);
   b) a nucleic acid sequence encoding alphavirus nonstructural proteins nsP1, nsP2, nsP3 and nsP4;
   c) a nucleic acid sequence encoding an alphavirus subgenomic promoter;
   d) a nucleic acid sequence encoding a second alphavirus 5' untranslated region (5' UTR) and 51 nucleotide conserved sequence element (51-nt CSE);
   e) a nucleic acid sequence encoding a protease;
   f) a nucleic acid sequence encoding a heterologous protein; and
   g) a nucleic acid sequence encoding an alphavirus 3' untranslated region (3' UTR).

2. The recombinant replicon nucleic acid of claim 1, wherein the nucleic acid sequence of (d) is modified to move all AUGs in the nucleic acid sequence into the same open reading frame as the initiating AUG.

3. The recombinant replicon nucleic acid of claim 1, wherein the protease is selected from the group consisting of a 2A protease from foot and mouth disease virus (FMDV), ubiquitin, a ubiquitin-like protein, Npro of pestiviruses and alphavirus capsid-encoded protease.

4. The recombinant replicon nucleic acid of claim 1, further comprising a nucleic acid sequence encoding an alphavirus capsid and the first 2 or more amino acids of E3 protein upstream of the nucleic acid sequence of (f).

5. A recombinant replicon nucleic acid comprising:
   a) a nucleic acid sequence encoding a first aiphavirus 5' untranslated region (5' UTR) and a 51 nucleotide conserved sequence element (51-nt CSE);
   b) a nucleic acid sequence encoding alphavirus nonstructural proteins nsP1, nsP2, ns P3 and nsP4;
   c) a nucleic acid sequence encoding a first alphavirus subgenomic promoter;
   d) a nucleic acid sequence encoding a second alphavirus 5' untranslated region (5' UTR) and a 51 nucleotide conserved sequence element (51-nt CSE);
   e) a nucleic acid sequence encoding a second alphavirus subgenomic promoter;
   f) a nucleic acid sequence encoding a heterologous protein; and
   g) a nucleic, acid sequence encoding an alphavirus 3' untranslated region (3' UTR).

6. A recombinant replicon nucleic acid comprising:
   a) a nucleic acid sequence encoding a first alphavirus 5' untranslated region (5' UTR) and a first 51 nucleotide conserved sequence element (51-nt CSE);
   b) a nucleic acid sequence encoding alphavirus nonstructural proteins nsP1, nsP2, nsP3 and nsP4;
   c) a nucleic acid sequence encoding a first alphavirus subgenomic promoter;
   d) a nucleic acid sequence encoding a second alphavirus 5' untranslated region (5' UTR) or a modified 5' UTR comprising a cellular Asp tRNA sequence, and a second 51 nucleotide conserved sequence element (51-nt CSE);
   e) a nucleic acid sequence encoding a second alphavirus subgenomic promoter;
   f) a nucleic acid sequence encoding a translational enhancer derived from an Old World alphavirus;
   g) a nucleic acid sequence encoding a protease;
   h) a nucleic acid sequence encoding a heterologous protein; and
   i) a nucleic acid sequence encoding an alphavirus 3' untranslated region (3' UTR).

7. The recombinant replicon nucleic acid of claim 6, wherein the protease is selected from the group consisting of a 2A protease from FMDV, ubiquitin, a ubiquitin-like protein, alphavirus capsid protein and Npro of pestiviruses.

8. The recombinant replicon nucleic acid of claim 1, wherein the nucleic acid is RNA.

9. The recombinant replicon nucleic acid of claim 1, wherein the nucleic acid is DNA cloned under control of SP6, T7 or DNA-dependent RNA polymerase I or II.

10. An alphavirus particle comprising the recombinant replicon nucleic acid of claim 1.

11. A population of alphavirus particles, comprising the alphavirus particle of claim 10.

12. A composition comprising the population of claim 11 in a pharmaceutically acceptable carrier.

13. A composition comprising the recombinant replicon nucleic acid of claim 1, in a pharmaceutically acceptable carrier, 14. An isolated cell comprising the recombinant replicon nucleic acid of claim 1.

15. A method of producing a heterologous protein in a cell, comprising introducing the recombinant replicon nucleic acid of claim 1 into the cell under conditions whereby the nucleic acid sequence of (f) is expressed, wherein the cell is in a cell culture thereby producing the heterologous protein in the cell.

16. The method of claim 15, further comprising the step of harvesting the heterologons protein from the cell culture.

17. A method eliciting an immune response to a heterologous protein in a subject, comprising administering to the subject an immunogenic amount of the recombinant replicon nucleic acid of claim 1, thereby eliciting an immune response to the heterologous protein encoded by the nucleic acid sequence of (f).

18. A method of delivering a therapeutic heterologous protein to a subject, comprising administering to the subject a therapeutic amount of the recombinant replicon nucleic acid of claim 1, wherein the nucleic acid sequence of (f) encodes a therapeutic heterologous protein, thereby delivering a therapeutic heterologous protein to the subject.

19. A method of making infectious, defective alphavirus particles, comprising:
   a) introducing into a cell the following:
      (i) the recombinant replicon nucleic acid of claim 1; and
      (ii) one or more helper nucleic acids encoding alphavirus structural proteins,
      wherein the one or more helper nucleic acids produce all of the alphavirus structural proteins, and
   b) producing said alphavirus particles in the cell.

* * * * *

UNITED STATES PATENT AND TRADEMARK OFFICE
CERTIFICATE OF CORRECTION

| | | |
|---|---|---|
| PATENT NO. | : 8,961,995 B2 | Page 1 of 1 |
| APPLICATION NO. | : 13/789215 | |
| DATED | : February 24, 2015 | |
| INVENTOR(S) | : Frolov et al. | |

It is certified that error appears in the above-identified patent and that said Letters Patent is hereby corrected as shown below:

In the Specification:
Column 4, Line 6: Please correct "1)" to read -- f) --

Column 4, Line 17: Please correct "1)" to read -- f) --

In the Claims:
Column 26, Claim 5, Line 17: Please correct "alphavirus 5"
to read -- alphavirus 5' --

Column 26, Claim 5, Line 32: Please correct "a nucleic, acid"
to read -- a nucleic acid --

Signed and Sealed this
Twenty-fifth Day of August, 2015

Michelle K. Lee
*Director of the United States Patent and Trademark Office*